(12) United States Patent
Rothstein et al.

(10) Patent No.: US 10,695,172 B2
(45) Date of Patent: *Jun. 30, 2020

(54) TRANSCATHETER HEART VALVE REPLACEMENT SYSTEMS, HEART VALVE PROSTHESES, AND METHODS FOR PERCUTANEOUS HEART VALVE REPLACEMENT

(71) Applicant: Medtronic, Inc., Minneapolis, MN (US)

(72) Inventors: Paul Rothstein, Elk River, MN (US); Jeffrey Sandstrom, Scandia, MN (US)

(73) Assignee: Medtronic, Inc., Minneapolis, MN (US)

( * ) Notice: Subject to any disclaimer, the term of this patent is extended or adjusted under 35 U.S.C. 154(b) by 200 days.

This patent is subject to a terminal disclaimer.

(21) Appl. No.: 15/936,901

(22) Filed: Mar. 27, 2018

(65) Prior Publication Data

US 2018/0214264 A1    Aug. 2, 2018

Related U.S. Application Data

(63) Continuation of application No. 14/964,777, filed on Dec. 10, 2015, now Pat. No. 9,931,204.

(51) Int. Cl.
*A61F 2/24* (2006.01)
*A61F 2/95* (2013.01)

(52) U.S. Cl.
CPC .......... *A61F 2/2418* (2013.01); *A61F 2/243* (2013.01); *A61F 2/2409* (2013.01);
(Continued)

(58) Field of Classification Search
CPC ...... A61F 2/2418; A61F 2/2427; A61F 2/243; A61F 2/2409; A61F 2/2436; A61F 2250/001; A61F 2220/0008
See application file for complete search history.

(56) References Cited

U.S. PATENT DOCUMENTS 7,381,218 B2    6/2008   Schreck
7,959,672 B2    6/2011   Salahieh et al.
(Continued)

FOREIGN PATENT DOCUMENTS

| EP | 2 898 858 A1 | 7/2015 |
| WO | 2013/059743 A1 | 4/2013 |
| WO | 2015/173794 A1 | 11/2015 |

OTHER PUBLICATIONS

International Search Report and Written Opinion dated Mar. 6, 2017 in corresponding International Patent Application No. PCT/US2016/065314.

*Primary Examiner* — Julian W Woo
(74) *Attorney, Agent, or Firm* — Medler Ferro Woodhouse & Mills PLLC

(57) ABSTRACT

A transcatheter heart valve prosthesis configured in accordance herewith includes an expandable frame having a plurality of commissure posts extending therefrom, a radially expandable tubular component attached to the plurality of commissure posts, and a locking mechanism operably coupled to a wire. The wire is at least partially slideably disposed within a channel formed in a wall of the tubular component and the locking mechanism is configured to permit the wire to be advanced within the channel to thereby transition the tubular component into a deployed configuration that at least partially engages tissue at the native heart valve.

20 Claims, 15 Drawing Sheets

(52) U.S. Cl.
CPC .......... *A61F 2/2427* (2013.01); *A61F 2/2436* (2013.01); *A61F 2002/9517* (2013.01); *A61F 2220/0008* (2013.01); *A61F 2250/001* (2013.01); *A61F 2250/0004* (2013.01); *A61F 2250/0069* (2013.01)

(56) References Cited

U.S. PATENT DOCUMENTS

| | | | |
|---|---|---|---|
| 7,993,394 B2 * | 8/2011 | Hariton | A61F 2/2433 623/2.17 |
| 8,308,798 B2 | 11/2012 | Pintor et al. | |
| 8,460,368 B2 * | 6/2013 | Taylor | A61F 2/2418 623/2.11 |
| 9,675,452 B2 | 6/2017 | Valdez et al. | |
| 9,707,074 B2 | 7/2017 | Yang et al. | |
| 9,931,204 B2 * | 4/2018 | Rothstein | A61F 2/243 |
| 2005/0075729 A1 | 4/2005 | Nguyen et al. | |
| 2007/0265701 A1 | 11/2007 | Gurskis et al. | |
| 2008/0243245 A1 | 10/2008 | Thambar et al. | |
| 2009/0112309 A1 | 4/2009 | Jaramillo et al. | |

* cited by examiner

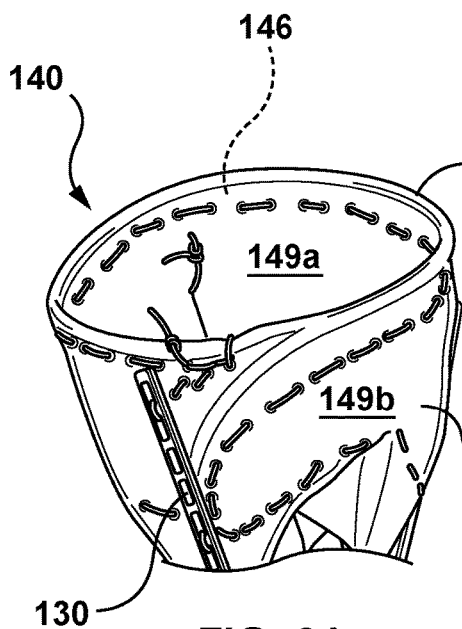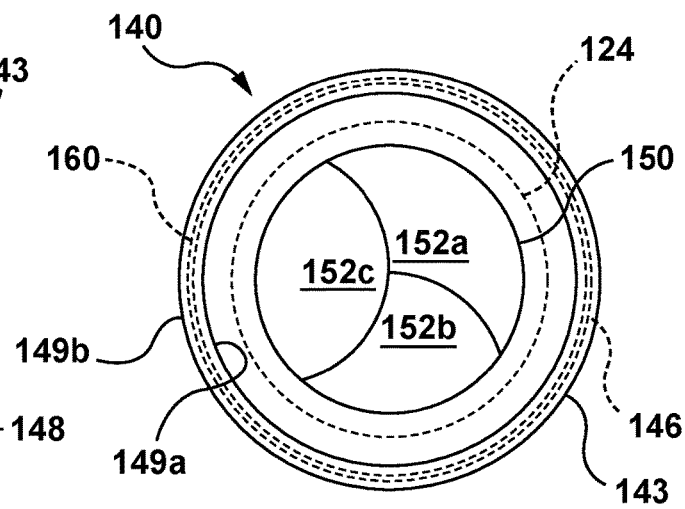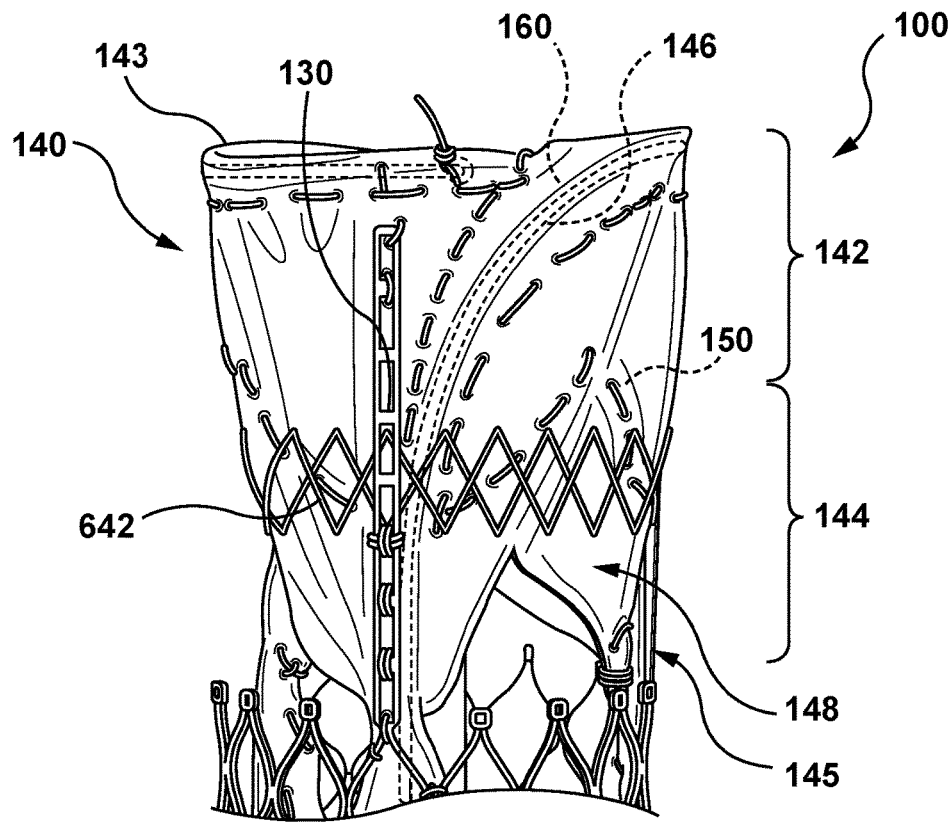
FIG. 6A
FIG. 6B
FIG. 6C

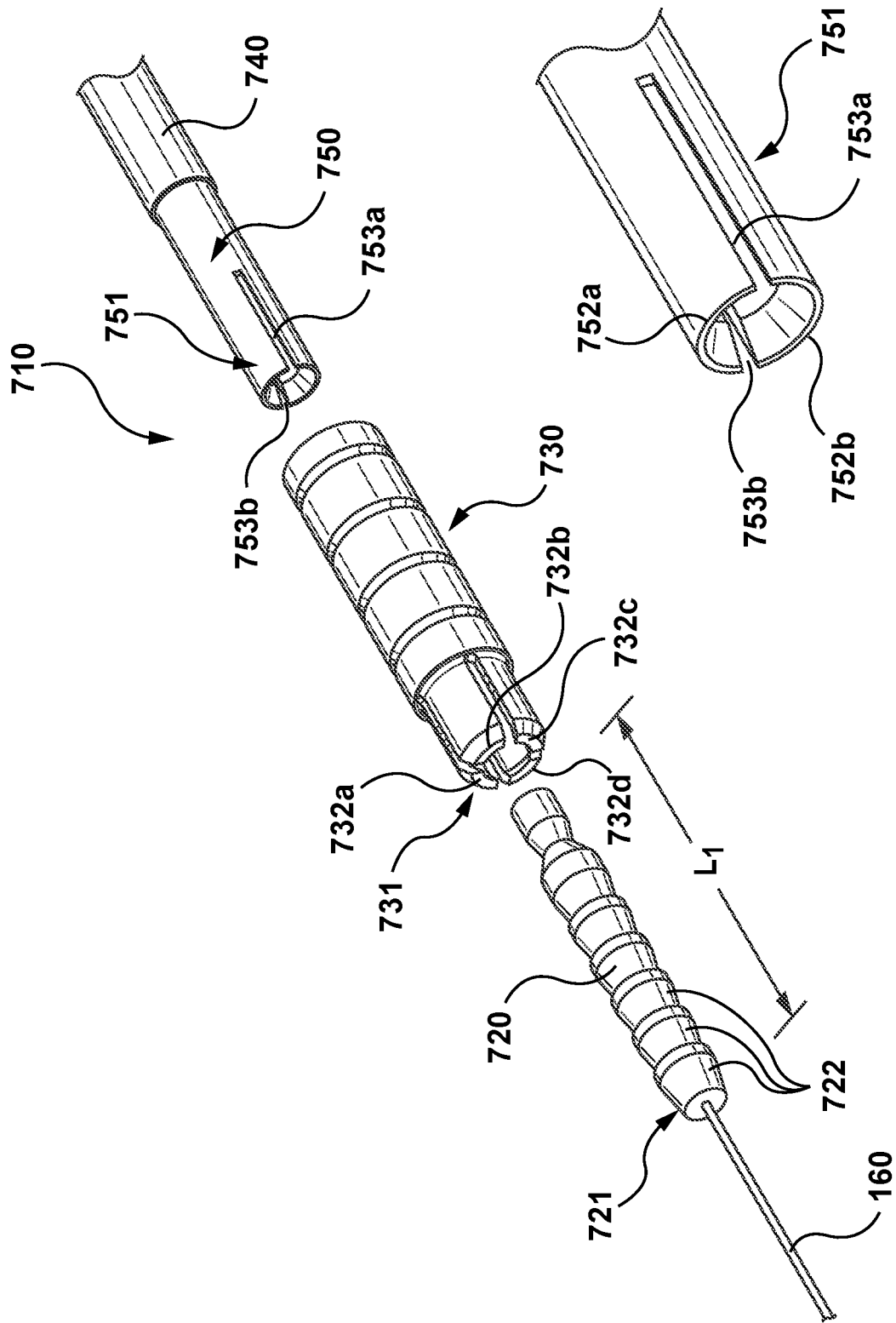

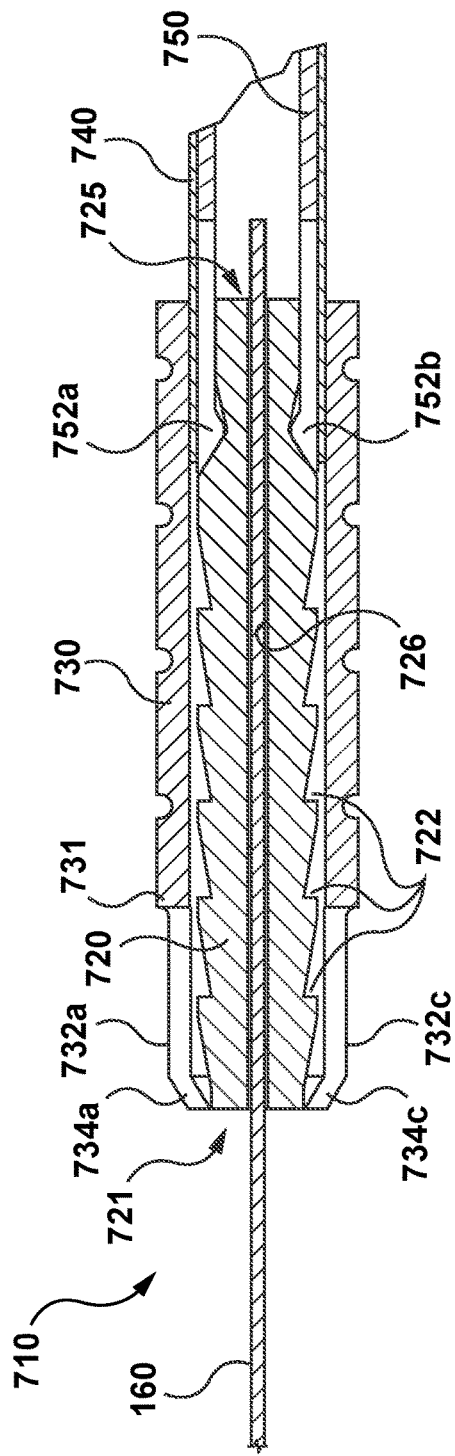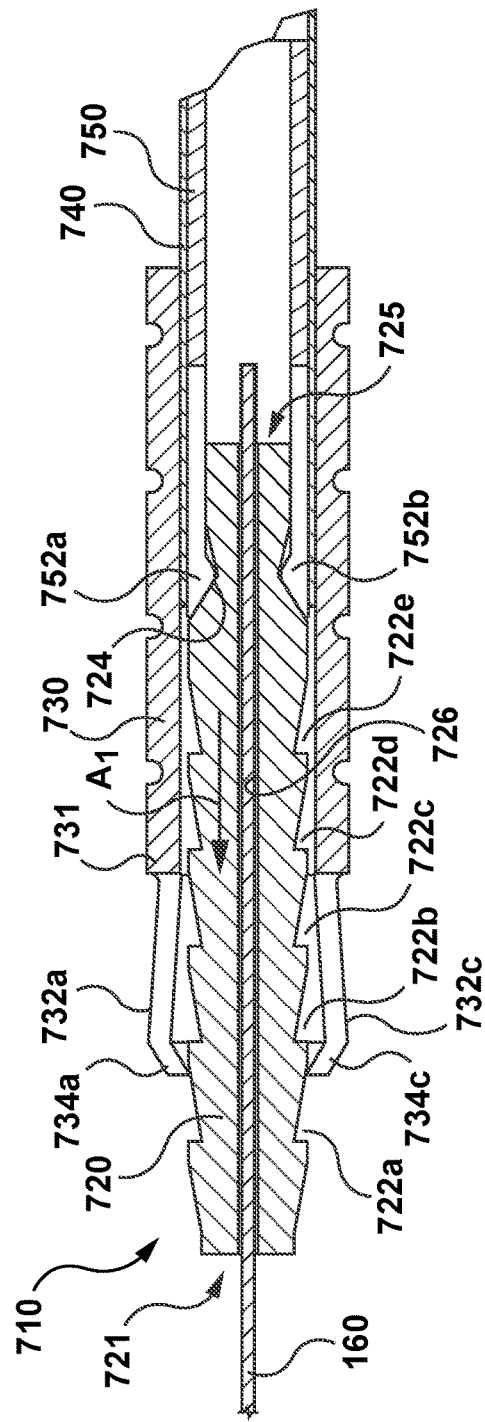
FIG. 8A
FIG. 8B

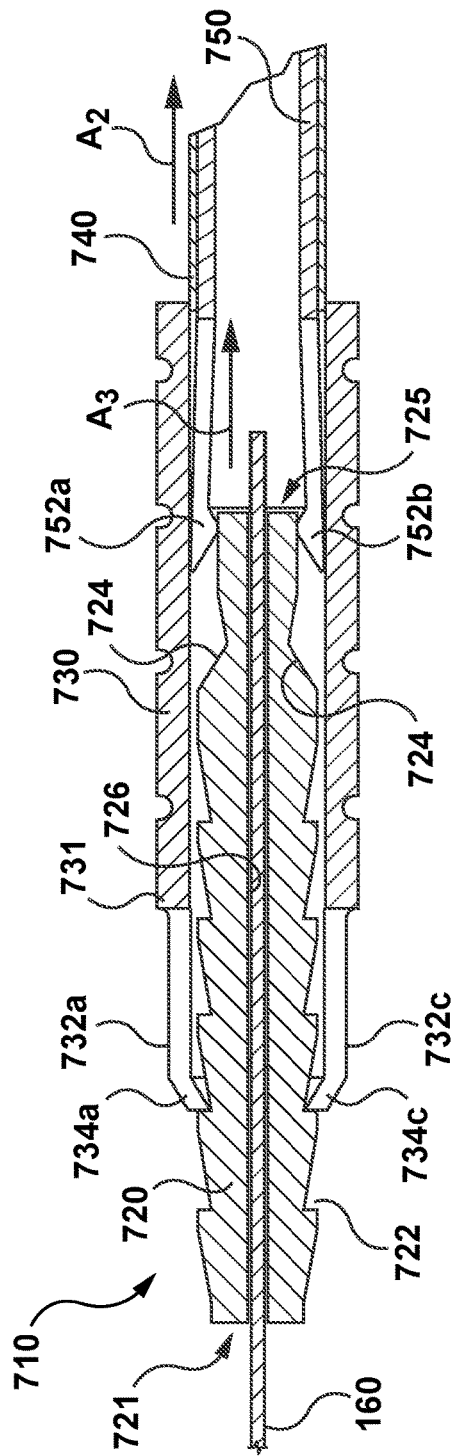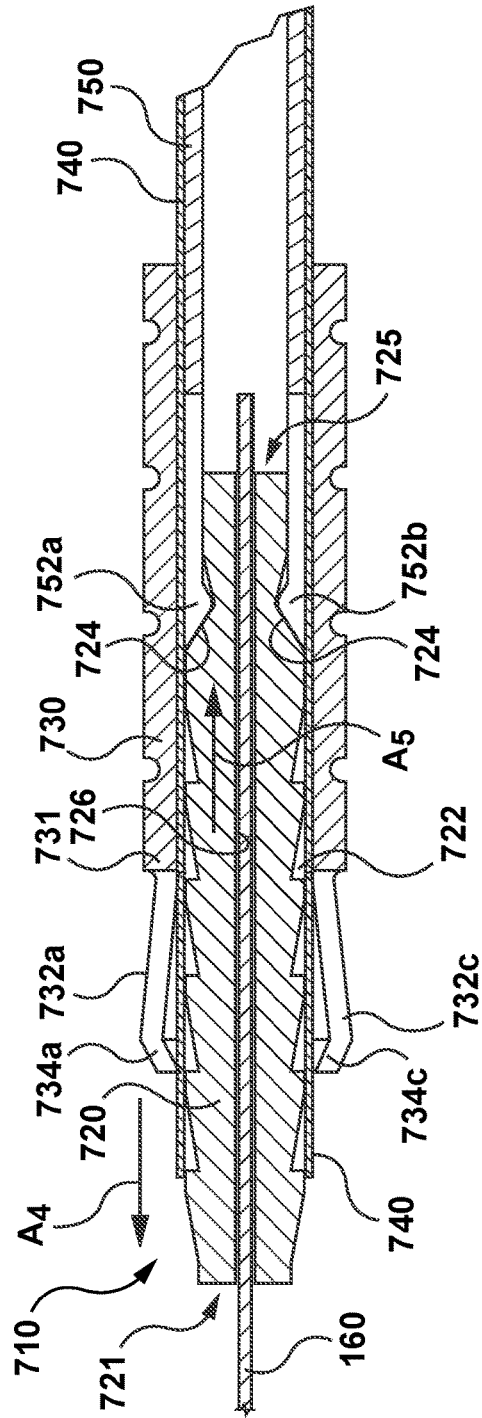
FIG. 8C
FIG. 8D

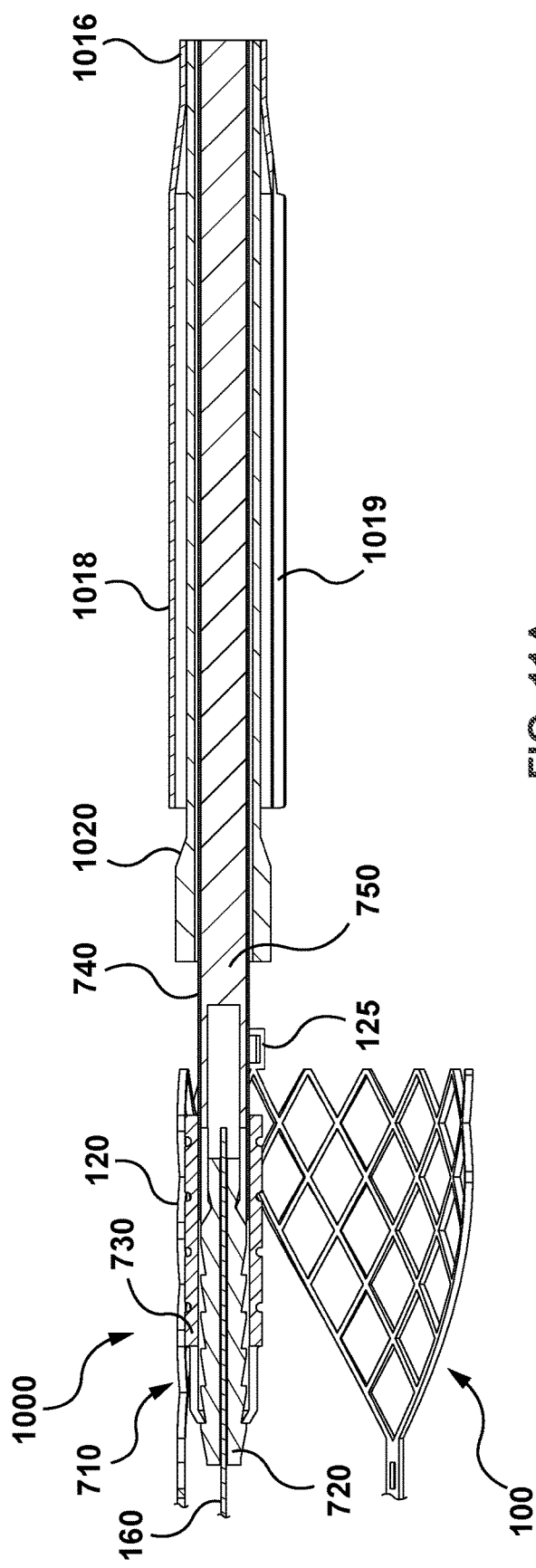
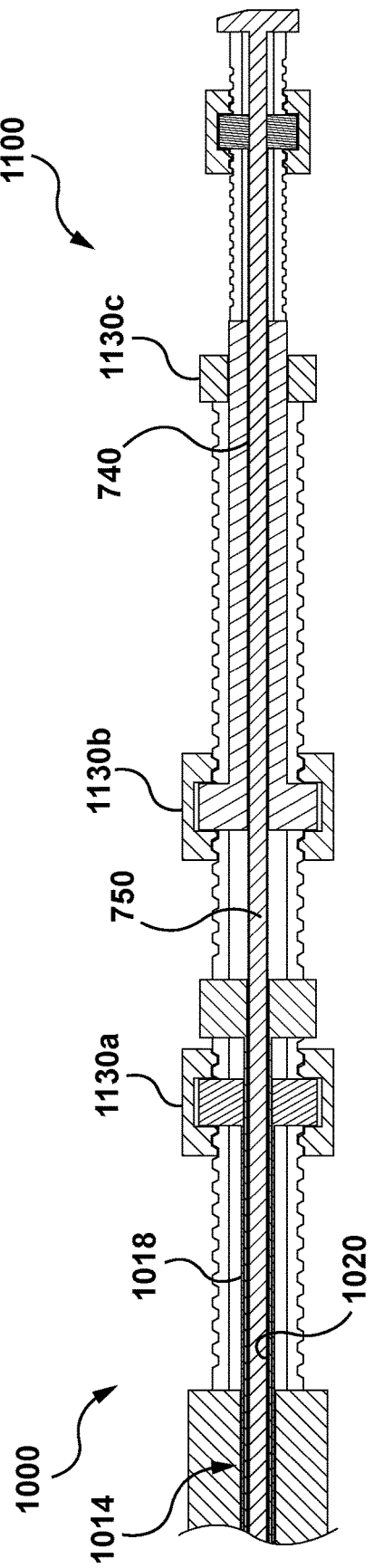
FIG. 11A
FIG. 11B

TRANSCATHETER HEART VALVE REPLACEMENT SYSTEMS, HEART VALVE PROSTHESES, AND METHODS FOR PERCUTANEOUS HEART VALVE REPLACEMENT

CROSS-REFERENCE TO RELATED APPLICATION

This application is a continuation of prior U.S. application Ser. No. 14/964,777, filed Dec. 10, 2015, now U.S. Pat. No. 9,931,204, the disclosure of which is incorporated by reference herein in its entirety.

FIELD OF THE INVENTION

The present technology relates generally to heart valve prostheses, transcatheter heart valve replacement systems and associated methods. In particular, several embodiments are directed to transcatheter heart valve systems and devices for percutaneous replacement of heart valves, such as an aortic valve.

BACKGROUND OF THE INVENTION

The human heart is a four chambered, muscular organ that provides blood circulation through the body during a cardiac cycle. The four main chambers include the right atria and right ventricle which supplies the pulmonary circulation, and the left atria and left ventricle which supplies oxygenated blood received from the lungs to the remaining body. To insure that blood flows in one direction through the heart, atrioventricular valves (tricuspid and mitral valves) are present between the junctions of the atria and the ventricles, and semi-lunar valves (pulmonary valve and aortic valve) govern the exits of the ventricles leading to the lungs and the rest of the body. These valves contain leaflets or cusps that open and shut in response to blood pressure changes caused by the contraction and relaxation of the heart chambers. The leaflets move apart from each other to open and allow blood to flow downstream of the valve, and coapt to close and prevent backflow or regurgitation in an upstream manner.

Diseases associated with heart valves, such as those caused by damage or a defect, can include stenosis and valvular insufficiency or regurgitation. For example, valvular stenosis causes the valve to become narrowed and hardened which can prevent blood flow to a downstream heart chamber or structure (e.g., aorta) to occur at the proper flow rate and cause the heart to work harder to pump the blood through the diseased valve. Aortic stenosis, for example, can lead to chest pain, fainting, and heart failure. Valvular insufficiency or regurgitation occurs when the valve does not close completely, allowing blood to flow backwards, thereby causing the heart to be less efficient. For example, aortic valvular insufficiency results in blood pooling in the left ventricle which must then expand its normal capacity to accommodate the pooled volume of blood as well as the new blood received in the subsequent cardiac cycle. For this reason the heart muscle must work harder to pump the extra volume of blood which causes strain of the heart muscle over time as well as raises the blood pressure in the heart. A diseased or damaged valve, which can be congenital, age-related, drug-induced, or in some instances, caused by infection, can result in an enlarged, thickened heart that loses elasticity and efficiency. Other symptoms of heart valve diseases, such as stenosis and valvular insufficiency, can include weakness, shortness of breath, dizziness, fainting, palpitations, anemia and edema, and blood clots which can increase the likelihood of stroke or pulmonary embolism. Such symptoms can often be severe enough to be debilitating and/or life threatening.

Prosthetic heart valves have been developed for repair and replacement of diseased and/or damaged heart valves. Such valves can be percutaneously delivered and deployed at the site of the diseased heart valve through catheter-based systems. Such prosthetic heart valves can be delivered while in a low-profile or compressed/contracted arrangement so that the prosthetic valves can be contained within a sheath component of a delivery catheter and advanced through the patient's vasculature. Once positioned at the treatment site, the prosthetic valves can be expanded to engage tissue at the diseased heart valve region to, for instance, hold the prosthetic valve in position. While these prosthetic valves offer minimally invasive methods for heart valve repair and/or replacement, challenges remain to provide prosthetic valves that prevent leakage between the implanted prosthetic valve and the surrounding tissue (paravalvular leakage) and for preventing movement and/or migration of the prosthetic valve that could occur during the cardiac cycle. For example, the repair or replacement of the aortic valve can present numerous challenges due to differing anatomies and etiologies presented by individual patients. The varying shapes, sizes and other features associated with an abnormal or unhealthy aortic valve can prevent proper alignment of the replacement (e.g., prosthetic) valve which can cause leakage, valve impingement or dislodgement of the prosthesis. In a particular example, stenosis of the aortic valve can deform the valvular area which can result in paravalvular leakage around an implanted replacement valve. Additional challenges can include providing a prosthetic valve that can be adjusted or repositioned during or after implantation and/or for replacing a previously implanted prosthetic valve.

BRIEF SUMMARY OF THE INVENTION

Embodiments hereof are directed to heart valve prostheses and methods of percutaneous implantation thereof. The heart valve prostheses have a compressed configuration for delivery via a vasculature or other body lumens to a native heart valve of a patient and an expanded configuration for deployment within the native heart valve. In an embodiment, the heart valve prosthesis may include an expandable frame defining a lumen through which blood may flow, the lumen extending from a first end to a second end thereof, wherein the frame includes a plurality of commissure posts extending from the first end. The prosthesis may also include an inflow member attached to the plurality of commissure posts. The inflow member has an upstream portion and a downstream portion and a channel formed in a wall thereof, wherein the channel extends from at least the downstream portion to the upstream portion, and wherein an interior of the inflow member is configured to support a prosthetic valve. The prosthesis may further include a locking mechanism secured within the lumen of the expandable frame and a wire operably coupled to the locking mechanism. The wire may be at least partially slideably disposed within the channel of the inflow member and the locking mechanism may be configured to permit the wire to be advanced within the channel of the inflow member to thereby transition the inflow member into a deployed configuration.

In another embodiment, a system for repair or replacement of a heart valve may include a prosthetic heart valve and a catheter assembly configured to delivery and deploy the prosthetic heart valve. In some embodiments, the prosthetic heart valve may have an anchoring structure and an inflow member coupled to and extending from the anchoring structure. The inflow member defines a lumen from an inflow end to an outflow end thereof. The inflow member may have a channel disposed within a wall thereof. The prosthetic heart valve may also include a prosthetic valve component disposed within the lumen of the inflow member. The prosthetic valve component can be configured to inhibit retrograde blood flow through the lumen. The prosthetic heart valve may further include an elongated stiffening element at least partially disposed within the channel of the inflow member to thereby transition the inflow member and the prosthetic valve component into a deployed configuration, and still further include a reversible ratcheting mechanism secured to the anchoring structure and coupled to the stiffening element. The catheter assembly may include a handle assembly having a first actuator for operating the reversible ratcheting mechanism to advance the stiffening element within the channel of the inflow member. The catheter assembly may also include an engagement tip extending from the handle assembly and configured to operatively engage the reversible ratcheting mechanism at a proximal end thereof upon actuation of the first actuator.

In yet another aspect, embodiments of the present technology provide a method of repairing or replacing a heart valve in a patient. In one embodiment, the method can include positioning a prosthetic device as described herein in a compressed configuration within a heart valve region of the patient. The method may also include releasing the prosthetic device to at least partially expand such that an inflow member extends through an annulus of the heart valve. The method may further include at least partially advancing a wire within a channel of the inflow member to transition the inflow member into a deployed configuration, and locking a position of the wire when the inflow member is in the deployed configuration.

BRIEF DESCRIPTION OF DRAWINGS

The foregoing and other features and aspects of the present technology can be better understood from the following description of embodiments and as illustrated in the accompanying drawings. The accompanying drawings, which are incorporated herein and form a part of the specification, further serve to illustrate the principles of the present technology. The components in the drawings are not necessarily to scale.

FIG. 6A is a perspective view of an inflow member of the heart valve prosthesis of FIG. 4 in accordance with an embodiment of the present technology.

FIG. 6B is a top view of the inflow member of the heart valve prosthesis of FIG. 4 in accordance with an embodiment of the present technology.

FIG. 6C is a side view of an inflow member in a deployed configuration and in accordance with an embodiment of the present technology.

FIG. 7 is an exploded view of a locking mechanism of a heart valve prosthesis in accordance with an embodiment of the present technology.

FIG. 7A is a perspective end view of an engagement tube of FIG. 7 in accordance with an embodiment of the present technology.

FIGS. 8A-8D are enlarged sectional views of a locking mechanism illustrating portions of a process for engaging the locking mechanism to deploy or retract the inflow member of the heart valve prosthesis of FIG. 4 in accordance with an embodiment of the present technology.

FIG. 11A is an enlarged sectional view of the portion A of the delivery system shown in FIG. 10 and in accordance with an embodiment of the present technology.

FIG. 11B is an enlarged sectional view of the portion B of the delivery system shown in FIG. 10 and in accordance with an embodiment of the present technology.

DETAILED DESCRIPTION OF THE INVENTION

Specific embodiments of the present technology are now described with reference to the figures, wherein like reference numbers indicate identical or functionally similar elements. The terms "distal" and "proximal" are used in the following description with respect to a position or direction relative to the treating clinician or with respect to a prosthetic heart valve device. For example, "distal" or "distally" are a position distant from or in a direction away from the clinician when referring to delivery procedures or along a vasculature. Likewise, "proximal" and "proximally" are a position near or in a direction toward the clinician. With respect to a prosthetic heart valve device, the terms "proximal" and "distal" can refer to the location of portions of the device with respect to the direction of blood flow. For example, proximal can refer to an upstream position or a position of blood inflow, and distal can refer to a downstream position or a position of blood outflow.

The following detailed description is merely exemplary in nature and is not intended to limit the present technology or the application and uses of the present technology. Although the description of embodiments hereof are in the context of treatment of heart valves and particularly an aortic valve, the present technology may also be used in any other body passageways where it is deemed useful. Furthermore, there is no intention to be bound by any expressed or implied theory presented in the preceding technical field, background, brief summary or the following detailed description.

Embodiments of the present technology as described herein can be combined in many ways to treat one or more of many valves of the body including valves of the heart such as the aortic valve. The embodiments of the present technology can be therapeutically combined with many known surgeries and procedures, for example, such embodiments can be combined with known methods of accessing the valves of the heart such as the aortic valve with antegrade or retrograde approaches, and combinations thereof.

Figure 1:
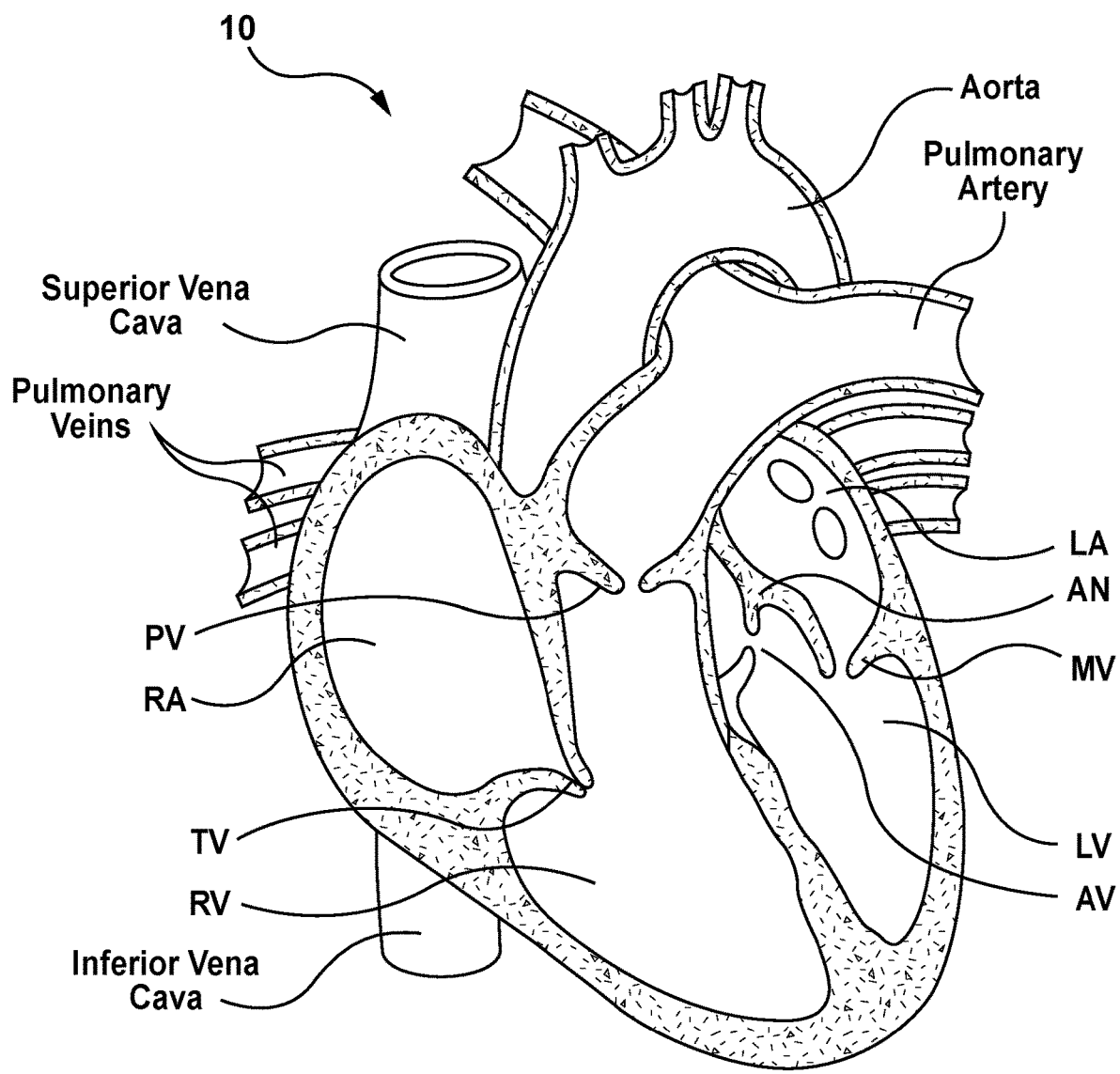
FIG. 1 is a schematic sectional illustration of a mammalian heart having native valve structures.
Figure 2A:
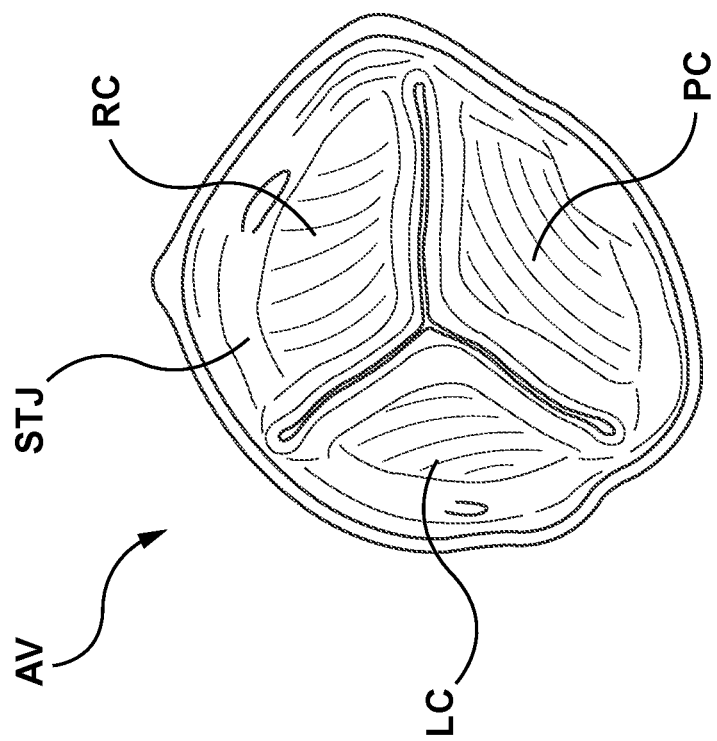
FIG. 2A is a schematic illustration of an inferior view of an aortic valve isolated from the surrounding heart structures and showing the annulus and native leaflets.

FIG. 1 is a schematic sectional illustration of a mammalian heart 10 that depicts the four heart chambers (right atria RA, right ventricle RV, left atria LA, left ventricle LV) and native valve structures (tricuspid valve TV, mitral valve MV, pulmonary valve PV, aortic valve AV). FIG. 2A is a schematic illustration of an inferior view of an aortic valve isolated from the surrounding heart structures and showing the annulus AN and native cusps or leaflets. Referring to FIGS. 1 and 2A together, the heart 10 comprises the left atrium LA that receives oxygenated blood from the lungs via the pulmonary veins. The left atrium LA pumps the oxygenated blood through the mitral valve MV and into the left ventricle LV during ventricular diastole. The left ventricle LV contracts during systole and blood flows outwardly through the aortic valve AV, into the aorta and to the remainder of the body.

Figure 2B:
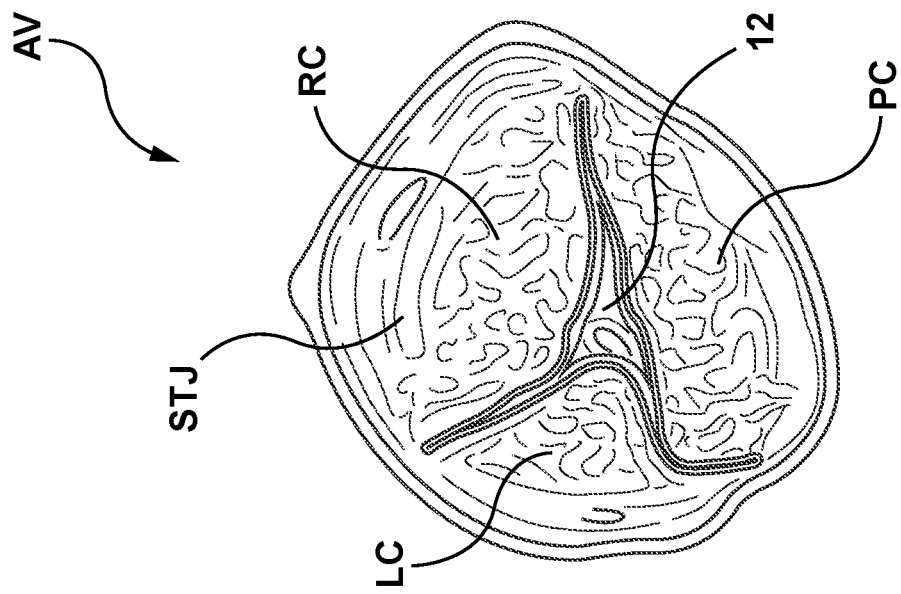
FIG. 2B is a schematic illustration of an inferior view of a stenotic aortic valve isolated from the surrounding heart structures and showing the annulus and native leaflets.

In a healthy heart, the cusps (e.g., leaflets) of the aortic valve AV meet evenly at the free edges or "coapt" to close (FIG. 2A) and prevent back flow of blood from the Aorta. Referring to FIG. 2A, the right cusp RC, the left cusp LC and the posterior cusp PC attach to the surrounding wall of the aorta at the sinotubular junction STJ above a fibrous ring of connective tissue called an annulus AN (FIG. 1). The flexible tissue of the aortic cusps (individually identified as RC, LC, and PC) open freely during left ventricle LV contraction to allow the blood to leave the heart chamber and be distributed systemically to the body's tissues. In a heart 10 having aortic valve stenosis, the aortic valve AV has narrowed causing the cusps (RC, LC, PC) to not sufficiently coapt or meet thereby forming a gap 12, as shown in FIG. 2B, that allows blood to back flow into the left ventricle LV. As such, aortic stenosis often results in a heart murmur that can be assessed by ultrasound. Typically, stenosis of the aortic valve AV prevents the valve from opening properly, forcing the heart muscle to work harder to pump blood through the valve. This can cause pooling of blood and pressure to build up in the left ventricle LV, which can thicken the heart muscle. One cause of valve stenosis includes progressive calcification of the valve (e.g., the aortic valve) which causes thickening and hardening of the tissue. Other causes of stenosis can include congenital defects (e.g., bicuspid valve), results of infections such as rheumatic fever or endocarditis, and age-related hardening of valve tissues.

Embodiments of prosthetic heart valve devices, delivery systems and associated methods in accordance with the present technology are described in this section with reference to FIGS. 3-12. It will be appreciated that specific elements, substructures, uses, advantages, and/or other aspects of the embodiments described herein and with reference to FIGS. 3-12 can be suitably interchanged, substituted or otherwise configured with one another in accordance with additional embodiments of the present technology.

Selected Embodiments of Prosthetic Heart Valve Systems and Devices

Figure 3:
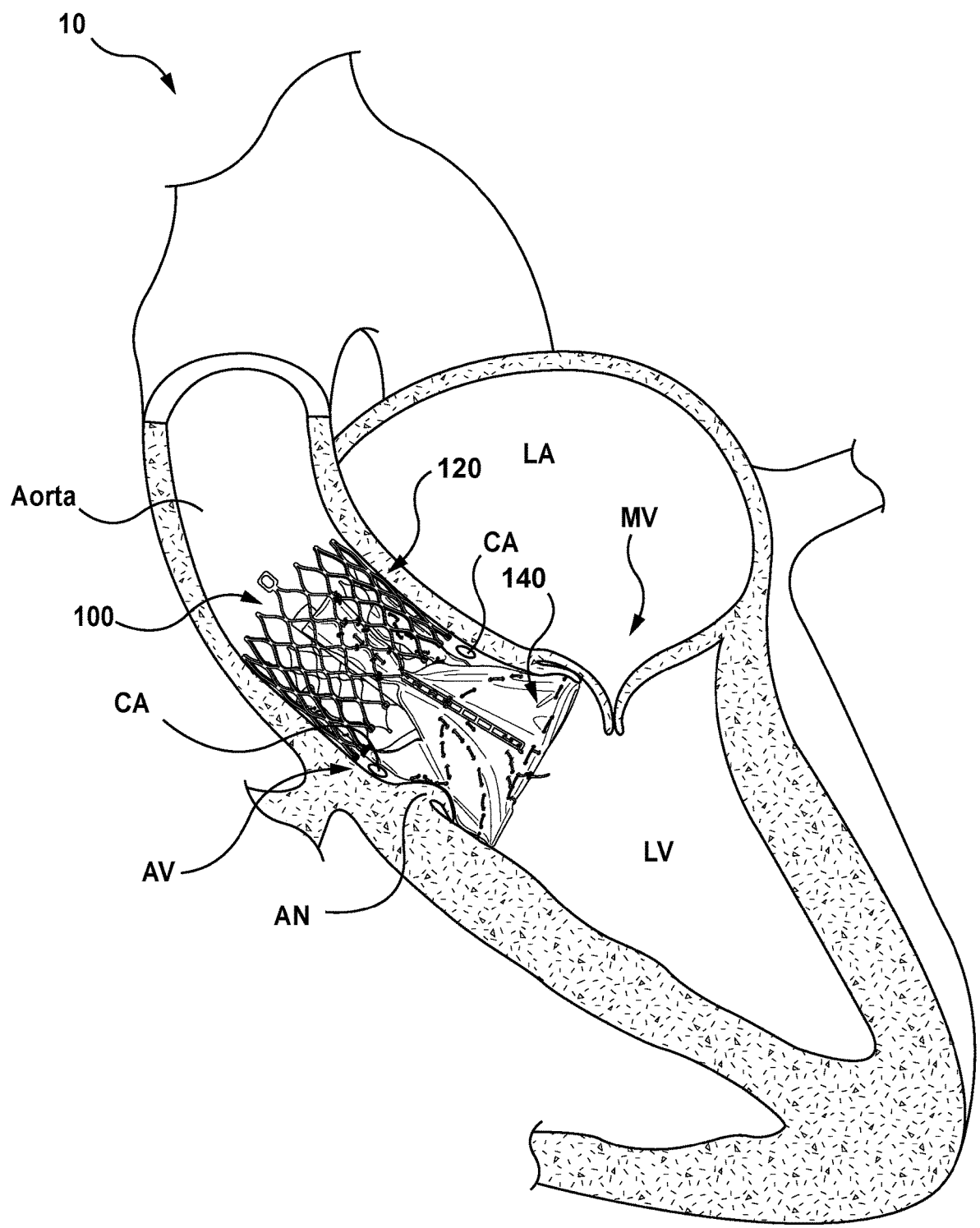
FIG. 3 illustrates a cut-away view of a heart showing a partial side view of a heart valve prosthesis implanted at a native aortic valve in accordance with an embodiment of the present technology.

Provided herein are systems, devices and methods suitable for percutaneous delivery and implantation of prosthetic heart valves in a heart of a patient. In some embodiments, methods and devices are presented for the treatment of valve disease by minimally invasive implantation of artificial or prosthetic heart valves. For example, a prosthetic heart valve device, in accordance with embodiments described herein, can be implanted for replacement of a diseased or damaged native aortic valve or prior implanted prosthetic aortic valve in a patient, such as in a patient suffering from aortic valve stenosis illustrated in FIG. 2B. In further embodiments, the device is suitable for implantation and replacement of other diseased or damaged heart valves or prior implanted prosthetic heart valves, such as tricuspid, pulmonary and mitral heart valves. FIG. 3 illustrates a cut-away view of a heart 10 showing a partial side view of a heart valve prosthesis or a prosthetic heart valve device 100 implanted at a native aortic valve AV in accordance with an embodiment of the present technology.

Figure 4:
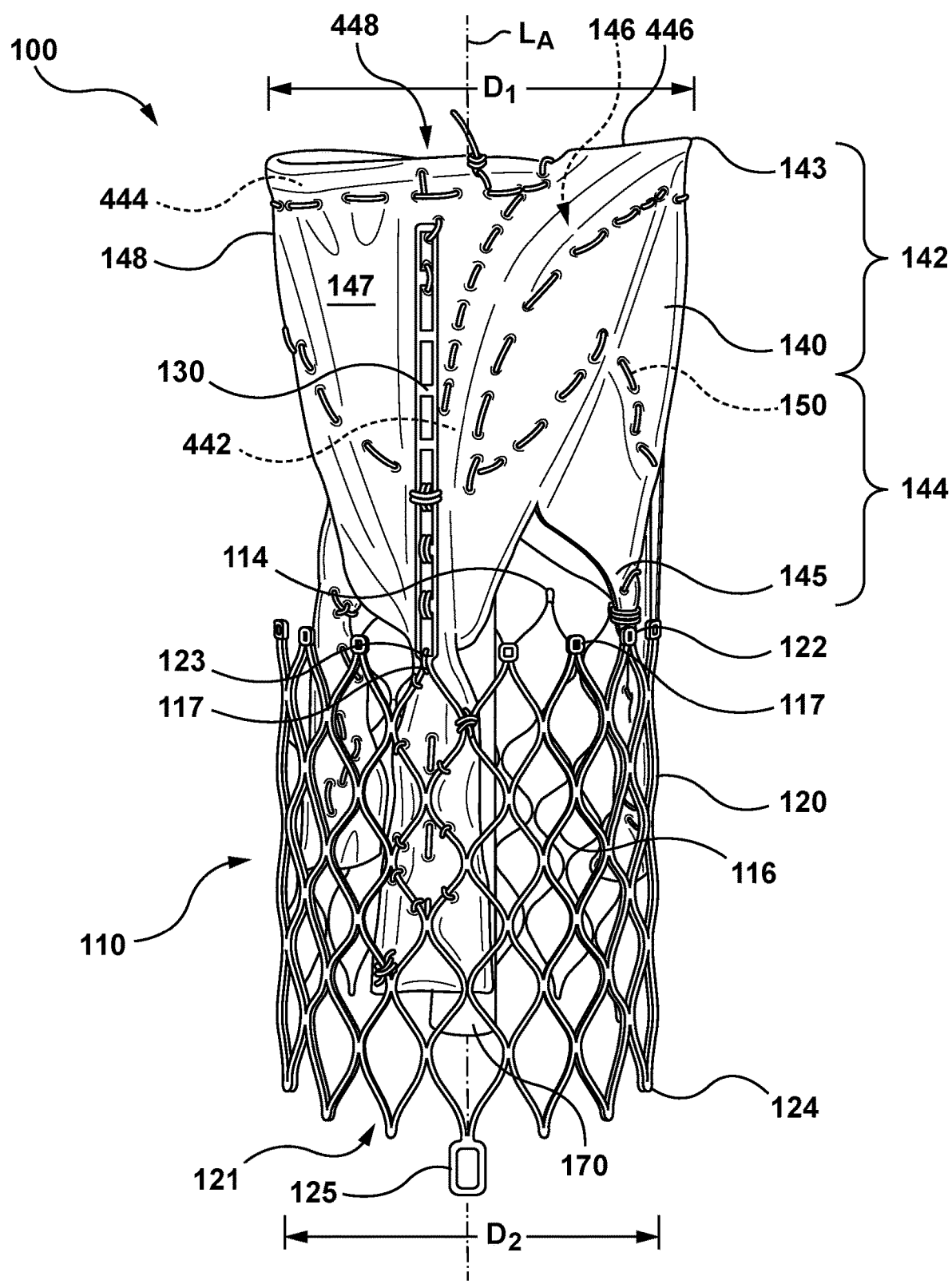
FIG. 4 is a side view of a heart valve prosthesis in a deployed or expanded configuration (e.g., a deployed state) in accordance with an embodiment of the present technology.
Figure 5A:
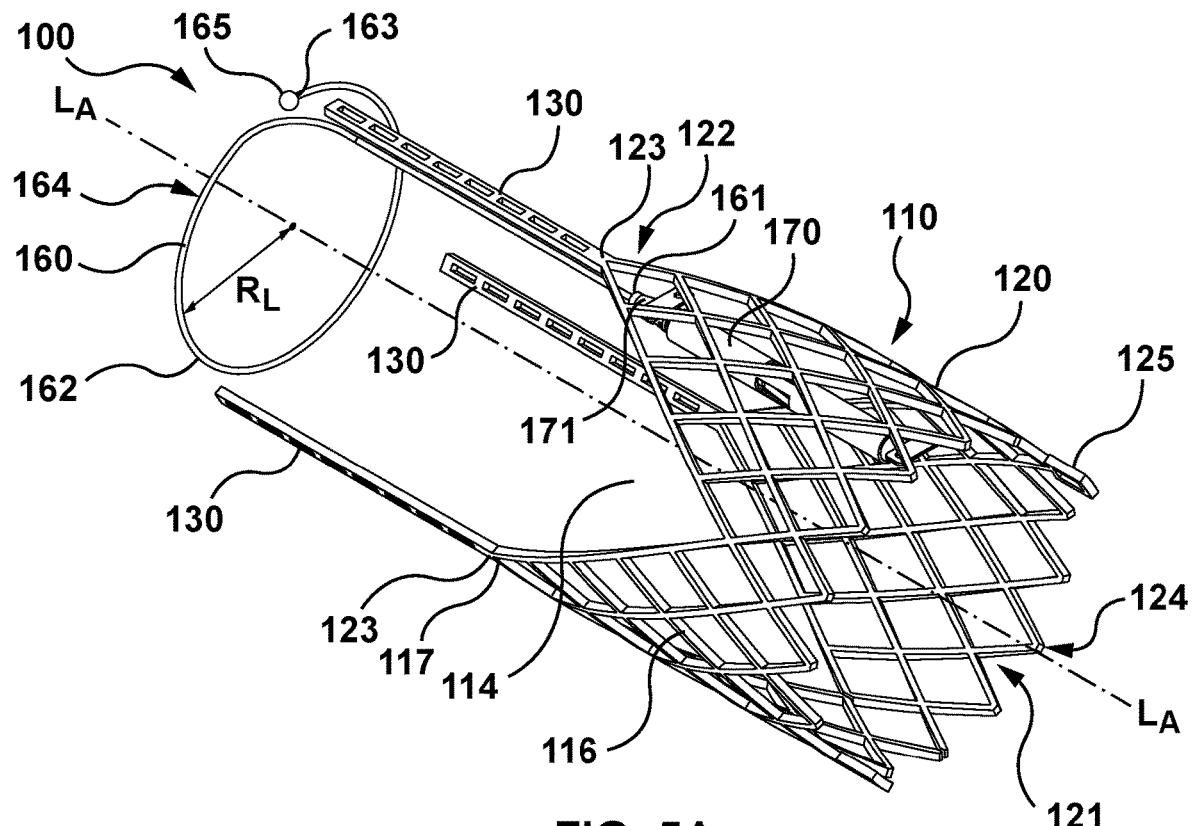
FIGS. 5A-5C are perspective side views of portions of a heart valve prosthesis in accordance with various embodiments of the present technology.
Figure 5B:
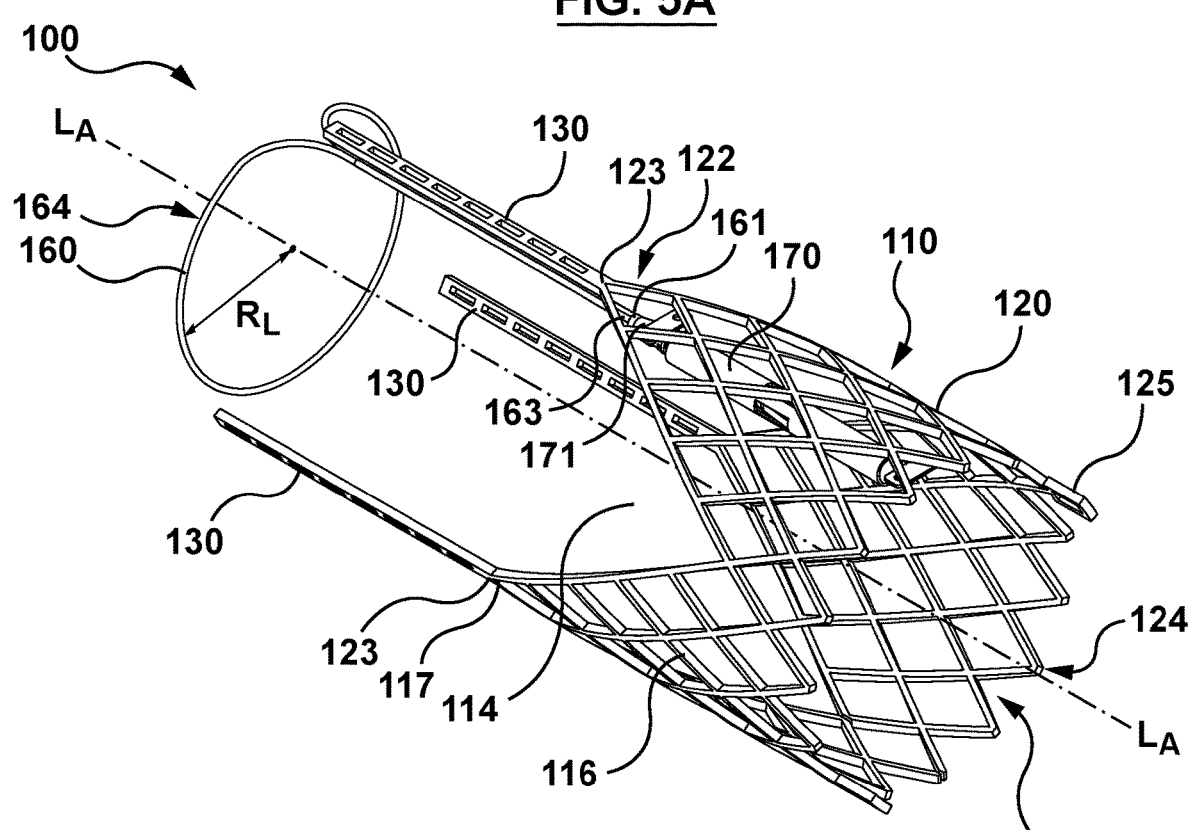
Figure 5C:
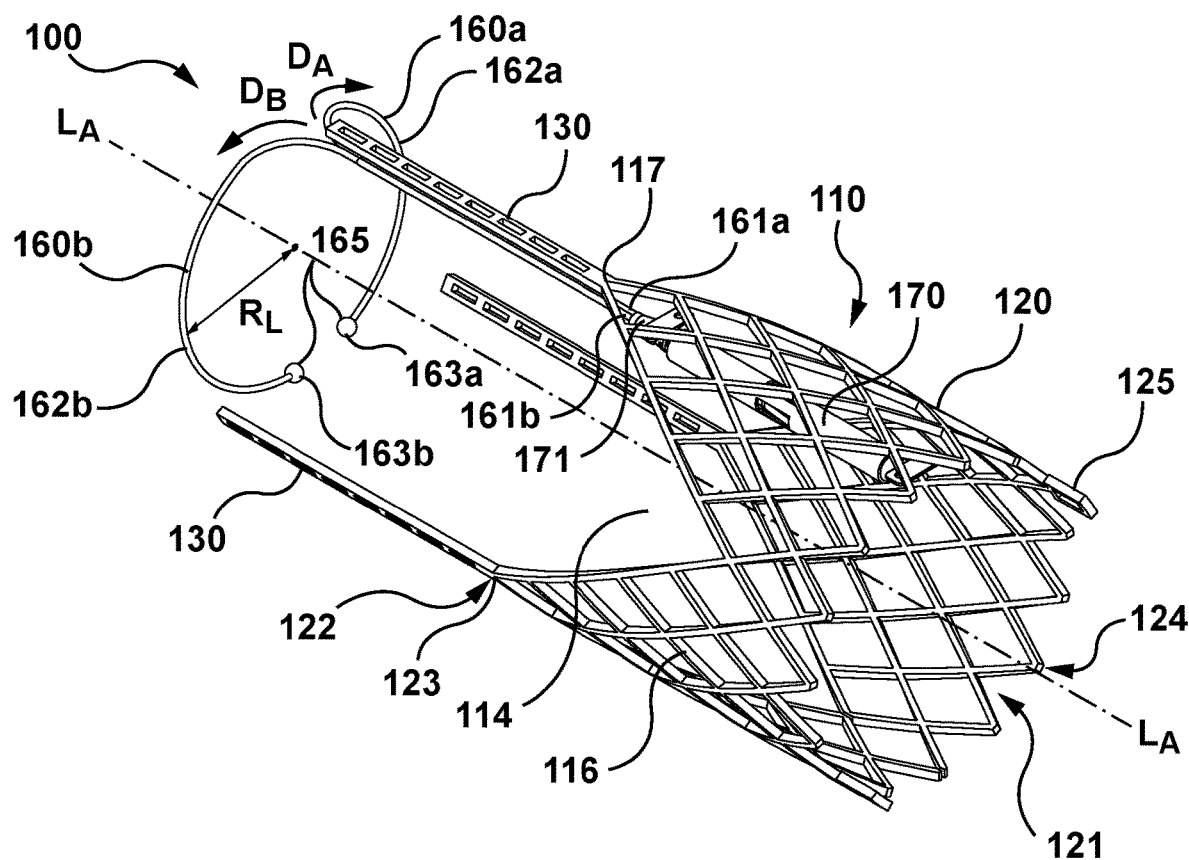

FIG. 4 is a side view of the heart valve prosthesis 100 in a radially expanded or deployed configuration (e.g., a deployed state) in accordance with an embodiment of the present technology. FIGS. 5A-5C are perspective side views of portions of the heart valve prosthesis 100 in accordance with various embodiments of the present technology. Referring to FIGS. 3-5C together, the heart valve prosthesis 100 includes a frame 110 or expandable structural support that includes a generally cylindrically-shaped anchoring structure 120 (e.g., an anchoring stent) that defines a lumen 121 through which blood can flow. As shown in FIGS. 4-5C, the anchoring structure 120 has a first end 122 and a second end 124 that are oriented along a longitudinal axis $L_A$ of the prosthesis 100 (FIG. 4). The frame 110 further includes one or more commissure posts 130 extending from the first end 122 and generally in an upstream direction from the anchoring structure 120 (e.g., to extend through the aortic valve AV and at least partially within the left ventricle LV). Additionally, the anchoring structure 120 can have a plurality of coupling features 125, such as eyelets, around the second end 124 to facilitate loading, retention and deployment of the prosthesis 100 within and from a delivery catheter (not shown) as further described herein.

Coupled to the commissure posts 130 is an inflow member or component 140 that is generally tubular in shape and has an interior 141 for retaining, holding and/or securing a prosthetic valve component 150 (shown as dotted lines in FIG. 4) therein. In embodiments in accordance herewith, and as explained in considerable detail below, the inflow member 140 may be radially expanded or collapsed in a manner similar to a tent, i.e., by advancing or positioning a support within the inflow member 140 or by retracting or removing the support from the inflow member 140.

As illustrated in FIG. 4, the inflow member 140 has an upstream portion 142 at an inflow end 143 that provides an opening to the interior 141, and has a downstream portion 144 at an outflow end 145 that are oriented along the longitudinal axis $L_A$ of the prosthesis 100. Generally, when implanted (FIG. 3), the upstream portion 142 of the inflow member 140 is oriented to receive blood inflow from a first heart chamber (e.g., left ventricle, left atrium), and the downstream portion 144 is oriented to release blood outflow into a second heart structure or chamber (e.g., aorta or left ventricle). As blood exits the downstream portion 144 of the inflow member 140, blood flow continues through the lumen 121 of the anchoring structure 120 and/or through side portals 114 (e.g., removed portions, cut-away portions, etc.) of the prosthesis 100 formed in the inflow member 140 (FIG.

4) and/or at or near the first end 122 of the anchoring structure 120 (FIGS. 5A-5C) to exit the heart 10 via the right and left coronary arteries CA (FIG. 3).

Referring to FIGS. 4-5C together, the inflow member 140 is reversibly expanded or collapsed with one or more elongated stiffening elements or wires 160 (FIGS. 5A-5C) that are at least partially disposed within a channel 146 formed within a wall 147 of the inflow portion 140 (FIG. 4). Accordingly as previously stated, the inflow member 140 is an expandable tube or tent-like structure that can be erected or collapsed by advancing or retracting the wires 160, respectively. Referring to FIGS. 4, 6A and 6B, the inflow member 140 includes a flexible sheet 148 that has an inner layer 149a and an opposing outer layer 149b that sandwich the wire(s) 160 therebetween at the inflow end 143 and, in one embodiment, between which the channel 146 can be defined. The flexible sheet 148 can be a sealing material that provides the inner layer 149a and/or the outer layer 149b to prevent leakage of blood (e.g., paravalvular leakage) between the implanted prosthesis 100 and the native heart tissue.

In one embodiment, the frame 110 can be a flexible metal frame or support structure having a plurality of ribs and/or struts 116 geometrically arranged to provide a latticework capable of being radially compressed (e.g., in a delivery state, not shown) for delivery to a target native valve site, and capable of radially expanding (e.g., to the radially expanded configuration shown in FIGS. 4-5C) for deployment and implantation at the target native valve site. Referring to the anchoring structure 120 shown in FIGS. 4-5C, the struts 116 can be arranged in a plurality of geometrical patterns that can expand or flex and contract while providing sufficient resilience and strength for maintaining position of the prosthetic 100 with respect to the native anatomy of the heart. For example, the struts 116 can be arranged in a circumferential pattern about the longitudinal axis $L_A$, wherein the circumferential pattern includes a series of diamond, zig-zagged, sinusoidal, or other geometric shapes.

In some embodiments described herein, and in order to transform or self-expand between an initial compressed configuration (e.g., in a delivery state, not shown) and the deployed configuration (FIG. 4), the frame 110 is formed from a resilient or shape memory material, such as a nickel titanium alloy (e.g., nitinol), that has a mechanical memory to return to the deployed or expanded configuration. In one embodiment, the frame 110 can be a unitary structure that defines the anchor structure 120 and the commissure posts 130 (FIGS. 5A-5C) to which the flexible sheet 148 and/or wire(s) 160 of the inflow member 140 attach. The frame 110 so described may be made from stainless steel, a pseudo-elastic metal such as nickel titanium alloy or nitinol, or a so-called super alloy, which may have a base metal of nickel, cobalt, chromium, or other metal. In some arrangements, the frame 110 can be formed as a unitary structure, for example, from a laser cut, fenestrated, nitinol or other metal tube. Mechanical memory may be imparted to the structure that forms the frame 110 by thermal treatment to achieve a spring temper in the stainless steel, for example, or to set a shape memory in a susceptible metal alloy, such as nitinol. The frame 110 may also include polymers or combinations of metals, polymers or other materials. In an alternative embodiment, the anchoring structure 120 can be a balloon-expandable tubular metal stent.

In other embodiments, the frame 110 can include separately manufactured components that are coupled, linked, welded, or otherwise mechanically attached to one another to form the frame 110. For example, the commissure posts 130 can be coupled at or near to the first end 122 of the anchoring structure 120 (e.g., at attachments points 123 on the struts 116 as defined by a diamond-shaped geometry of the anchoring structure 120). In particular embodiments, and as shown in FIG. 4, the commissure posts 130 and the anchoring structure 120 may be coupled by a variety of methods known in the art, e.g., soldering, welding, bonding, rivets or other fasteners, mechanical interlocking, or any combination thereof. Other arrangements and attachment points are contemplated for coupling a locking mechanism 170 and/or slideably coupling the wire(s) 160 within the lumen 121 of the anchoring structure 120, as described in more detail herein.

FIGS. 4-5C show the commissure posts 130 extending from the first end 122 of the anchoring structure 120. As illustrated, the commissure posts 130 are arranged or spaced relatively evenly about a circumference of the anchoring structure 120, and individual commissure posts 130 join adjacent struts 116 at a tip or crown 117, which in some embodiments can be the attachment point 123. In one embodiment, the tips 117 can be atraumatic in order to prevent injury to the cardiac tissue during deployment and through the cardiac cycle. In other arrangements, the commissure posts 130 can be unevenly distributed about a circumference of the anchoring structure 120.

As illustrated in FIG. 3, the inflow member 140 can engage tissue within the left ventricle LV on or above the fibrous annular ring (e.g., aortic annulus) demarking the junction of the aortic valve and the ventricular septum when implanted within a native aortic valve space. In this embodiment, the anchoring structure 120 can retain the inflow member 140 in a desired position within the native aortic valve and the inflow member 140 can adjustably expand to provide a desired radial force against native tissue and/or against prior implanted prosthetic surfaces to prevent paravalvular leakage and to retain the prosthetic valve component 150 in a desired position within the native valve region (e.g., between the native cusps and annulus of the aortic valve).

When deployed, the inflow member 140 and anchoring structure 120 are shown having generally circular cross-sectional shapes with the inflow member 140 having a cross-sectional dimension $D_1$ that is greater than a cross-sectional dimension $D_2$ of the anchoring structure 120 (FIG. 4). In some embodiments, the inflow member 140, the anchoring structure 120 or both can have other cross-sectional shapes, such as to accommodate deformations in the native aortic valve (e.g., bicuspid aortic valve, calcification, thickening, etc.) or the D-shaped mitral valve. For example, the inflow member 140 and/or anchoring structure 120 may expand to an irregular, non-cylindrical, or oval-shaped configuration for accommodating such deformations (e.g., congenital and/or disease-related deformations) or for accommodating the mitral valve. Furthermore, the native valves (e.g., aortic, mitral) can be uniquely sized and/or have other unique anatomical shapes and features that vary between patients, and the prosthesis 100 for replacing or repairing such valves can be suitable for adapting to the size, geometry and other anatomical features of such native valves. For example, the inflow member 140 can expand within the native heart valve region while simultaneously being flexible so as to conform to the region engaged by the inflow member 140.

FIGS. 6A and 6B are a perspective view and a top view, respectively, of the inflow member 140 of the prosthesis 100 illustrated in FIG. 4 and in accordance with an embodiment of the present technology. FIG. 6C is a side view of an inflow member 140 of the prosthesis 100 in accordance with an additional embodiment of the present technology. As illustrated in FIGS. 4 and 6A-6C, the inflow member 140 has the downstream portion 144 and the upstream portion 142 opposite the downstream portion 144 relative to the longitudinal axis $L_A$ of the prosthesis 100. The upstream portion 142 of the inflow member 140 can be a generally outward oriented portion of the prosthesis 100, as shown. In one embodiment, the inflow member 140 has a frusto-conical shape. In another embodiment, the downstream portion 144 can be substantially circular in cross-section while the upstream portion 142 can be generally circular or non-circular. In various arrangements, the cross-sectional shape of the upstream portion 142 can be imparted by the shape of the wire(s) 160 (shown in dotted lines in FIGS. 6B and 6C) as described further herein. Optionally, the inflow member 140 can include one or more resiliently deformable and flexible circumferential ribs 642 which, in some embodiments, can form a zig-zag, diamond or other pattern ring (FIG. 6C). The circumferential ribs 642 can provide additional radial force at the downstream portion 144 of the inflow member 140, and in some instances, additional support in the region of the inflow member 140 supporting the prosthetic valve component 150 therein.

As illustrated in FIG. 6B, the prosthetic valve component 150 may be coupled to the flexible sheet 148 within the interior 141 of the inflow member 140 for governing blood flow through the heart valve prosthesis 100. For example, the prosthetic valve component 150 can include a plurality of leaflets 152 (shown individually as 152a-c) that coapt and are configured to allow blood flow through the prosthesis 100 in a downstream direction (e.g., from the inflow end 143 of the inflow member 140 to the second end 124 of the anchoring structure 120) and inhibit blood flow in an upstream direction (e.g., from the outflow end 145 to the inflow end 143 of the inflow member 140). While the prosthetic valve component 150 is shown having a tricuspid arrangement, it is understood that the prosthetic valve component 150 can have two leaflets 152 (bicuspid arrangement, not shown) or more than three leaflets 152 that coapt to close the prosthetic valve component 150. In one embodiment, the leaflets 152 can be formed of bovine pericardium or other natural material (e.g., obtained from heart valves, aortic roots, aortic walls, aortic leaflets, pericardial tissue, such as pericardial patches, bypass grafts, blood vessels, intestinal submucosal tissue, umbilical tissue and the like from humans or animals) that are mounted to the flexible sheet 148 within the interior 141 of the radially-expanding inflow member 140. In another embodiment, synthetic materials suitable for use as valve leaflets 152 include DACRON® polyester (commercially available from Invista North America S.A.R.L. of Wilmington, DE), other cloth materials, nylon blends, polymeric materials, and vacuum deposition nitinol fabricated materials. In yet a further embodiment, valve leaflets 152 can be made of an ultra-high molecular weight polyethylene material commercially available under the trade designation DYNEEMA from Royal DSM of the Netherlands. With certain leaflet materials, it may be desirable to coat one or both sides of the leaflet with a material that will prevent or minimize overgrowth. It can be further desirable that the leaflet material is durable and not subject to stretching, deforming, or fatigue.

Referring to FIGS. 4 and 6A-6C together, the flexible sheet 148 can be a sheet of flexible material coupled to one or more commissure posts 130. In some embodiments the flexible sheet 148 can be folded flexible material that forms the opposing inner and outer layers 149a, 149b of the wall 147. In such embodiments, the channel 146 can be formed (e.g., via stitching, tape, staples, or other securing means) between the inner and outer layers 149a, 149b and thereby provide a path through which the wire(s) 160 can slideably move. The flexible sheet 148 can prevent paravalvular leakage as well as provide a medium for tissue ingrowth following implantation, which can further provide biomechanical retention of the prosthesis 100 in the desired deployment location within the native heart valve region. In some embodiments, the flexible sheet 148 or portions thereof may be a low-porosity woven fabric, such as polyester, DACRON® polyester, or polytetrafluoroethylene (PTFE), which creates a one-way fluid passage when attached to the frame 110 (e.g., the commissure posts 130). In one embodiment, the flexible sheet 148 or portions thereof may be a looser knit or woven fabric, such as a polyester or PTFE knit, which can be utilized when it is desired to provide a medium for tissue ingrowth and the ability for the fabric to stretch to conform to a curved surface. In another embodiment, polyester velour fabrics may alternatively be used for at least portions of the flexible sheet 148, such as when it is desired to provide a medium for tissue ingrowth on one side and a smooth surface on the other side. These and other appropriate cardiovascular fabrics are commercially available from Bard Peripheral Vascular, Inc. of Tempe, Ariz., for example. In another embodiment, the flexible sheet 148 or portions thereof may be a natural graft material, such as pericardium or another membranous tissue.

In addition to the inflow member 140 providing flexible material for preventing paravalvular leakage and/or tissue ingrowth, and in alternative embodiments, other portions of the prosthesis 100, such as the anchoring structure 120 and/or the commissure posts 130 may also be provided with a flexible material (not shown) to cover at least portions of surfaces thereof. Such materials may include those described herein or other materials that provide sealing, tissue ingrowth, and/or otherwise provide an atraumatic surface to engage native cardiac tissue.

In some embodiments, and as shown in the radially expanded configurations of FIGS. 4-5C, the prosthesis 100 also includes a locking mechanism 170 secured within the lumen 121 of the anchoring structure 120 and operably coupled to the wire(s) 160 for permitting the wire(s) to be advanced within the channel 146 (FIG. 4) of the inflow member 140 during implantation of the prosthesis 100. It should be understood that prior to being distally advanced within the channel 146 of inflow member 140 that the wire(s) 160 are substantially straight when positioned within a delivery system or catheter. The wire(s) 160 take the curved shapes shown in FIGS. 5A-5C when distally advanced into the channel 146 of inflow member 140. In other words, the channel 146 of inflow member 140 shapes or curves the wire(s) 160 as shown in FIGS. 5A-5C and the inflow member 140 is not shown in FIGS. 5A-5C for illustrative purposes only.

Referring to FIG. 5A, a first end 161 of the wire 160 is operably coupled to an upstream portion 171 of the locking mechanism 170, and the locking mechanism 170 is configured to permit the wire 160 to be advanced within the channel 146 (FIG. 4) of the inflow member 140 and thereby transition the inflow member 140 into a deployed configuration. When deployed, the wire 160 or other stiffening element is structurally independent of the anchoring structure 120 such that the wire 160 is radially deformable (e.g., for accommodating irregularly-shaped native anatomy, accommodating forces during the cardiac cycle, etc.) without substantially deforming the anchoring structure 120. Additionally, deformation of segments of the wire 160 providing structure at the inflow end is not translated to the downstream portion 144 of the inflow member 140 or the prosthetic valve component 150 housed therein.

In some embodiments, the wire 160 comprises shape memory material (e.g., nitinol) that can be pre-set to form a desired shape for radially expanding and providing support to the inflow member 140 when in an unbiased configuration. In another embodiment, the wire 160 can be formed of other metal or polymers or combinations thereof that may have mechanical or shape memory properties. In certain embodiments the wire(s) can be a single stranded wire while in alternative embodiments, the wire(s) 160 can be multi-stranded or braided wire(s). As described in more detail herein, the embodiments shown in FIGS. 5A and 5B illustrate arrangements of the prosthesis 100 having a single wire 160 distally advanceable to expand the inflow member 140 to the deployed configuration. FIG. 5C illustrates an arrangement having two wires 160a, 160b for expanding the inflow member 140 to the deployed configuration. Other arrangements can include more than two wires 160. For example, multiple wires can be advanced or retracted to provide the desired radial strength to the inflow member 140. More than one wire 160 can be advanced along the same path through the channel 146 of the flexible sheet 148. In other embodiments, multiple wires 160 can advance along different portions of the channel 146.

FIG. 5A illustrates an embodiment in which the wire 160 is advanced (e.g., by the locking mechanism 170) axially along a commissure post 130 followed by an arched portion 162. Referring to FIGS. 4 and 5A together, when the wire 160 is disposed within the channel 146 formed in the flexible sheet 148 of the inflow member 140 (FIG. 4), the wire 160 is advanced from the downstream portion 144 within a longitudinal segment 442 of the channel 146 to radially expand the arched portion 162 within a circumferential segment 444 of the channel 146 to thereby expand or form the inflow end 143 of the inflow member 140. In the illustrated embodiment, a second end 163 (e.g., distal end) of the wire 160 is advanced such that the arched portion 162 of the wire 160 forms a loop 164. When disposed within the channel 146 of the flexible sheet 148, as shown in FIG. 4, the wire 160 of FIG. 5A would at least partially surround an opening 446 of a lumen 448 at the inflow end 143 of the inflow member 140 thereby providing an expandable inlet into the prosthesis 100 and through which blood may flow following implantation. The second end 163 of the wire 160 may be advanced to several positions within the channel 146, for example within the circumferential segment 444 thereof, until a desired or effective loop radius $R_L$ is achieved. For example, a clinician may observe paravalvular leakage during implantation and continually and/or incrementally advance (or retract) the second end 163 of the wire 160 until the leakage is ceased. Accordingly, the loop radius $R_L$ may be increased or decreased by advancing or retracting the second end 163 of the wire 160 within the circumferential segment 444 of the channel 146, thereby providing an alterable or customizable component of the prosthesis 100 that can conform to a patient's unique anatomy in real-time during implantation. In certain embodiments, the second end 163 of the wire 160 may include an atraumatic tip 165 or other feature to inhibit penetration of the inner and/or outer layers 149a, 149b (FIGS. 6A and 6B) of the flexible sheet 148, the surrounding cardiac tissue during implantation, and/or to provide an anchoring point at which the wire can be secured within the channel 146 following deployment of the inflow member 140.

FIG. 5B illustrates another embodiment in which the first and second ends 161, 163 of the wire 160 are coupled to the locking mechanism 170. In this embodiment, a portion of the wire between the first and second ends 161, 163 is slideably disposed within the longitudinal and circumferential segments 442, 444 of the channel 146 (FIG. 4) to form a loop 164. In this embodiment, a loop radius $R_L$ may be increased or decreased by extending or retracting either or both of the first and second ends 161, 163 with respect to the upstream portion 171 of the locking mechanism 170. For example, in one embodiment, the second end 163 may be in a fixed position with respect to the upstream portion 171 and the first end 161 is moveable with respect to the upstream portion 171 to thereby increase or decrease the loop radius $R_L$ as desired. Likewise, the first end 161 may be in a fixed position and the second end 163 can be movable. In still other arrangements, the first and second ends 161, 163 may move in unison or separately to adjust the loop radius $R_L$. In operation, and when disposed within the channel 146 of the flexible sheet 148 of the inflow member 140 (FIG. 4), the wire 160 can be extended distally from the locking mechanism 170 to increase the loop radius $R_L$ within the circumferential segment 444 of the channel 146, thereby radially extending the inflow end 143 at the upstream portion 144 of the inflow member 140.

In yet another embodiment, illustrated in FIG. 5C, the prosthesis 100 has first and second wires 160a, 160b coupled to the locking mechanism 170. In this embodiment, each of the first ends 161a, 161b of the wires 160a, 160b are coupled to the upstream portion 171 of the locking mechanism 170, and when disposed within the channel 146 of the flexible sheet 148 (FIG. 4), the second ends 163a, 163b of the wires 160a, 160b would at least partially surround the opening 446 of the lumen 448 at the inflow end 143 of the inflow member 140. Referring to FIGS. 4 and 5C together, the second ends 163a, 163b can advance within the longitudinal segment 442 of the channel 146 (e.g., as the wires 160a, 160b advance distally along the commissure post 130), however, the first and second wires 160a, 160b diverge where the longitudinal segment 442 junctures with the circumferential segment 444. More particularly, an arched portion 162a of the first wire 160a advances at the juncture in a first direction $D_A$ and an arched portion 162b of the second wire 160b advances at the juncture in a second direction $D_B$. In other words during operation, the first and second wires 160a, 160b diverge where the longitudinal segment 442 segues to the circumferential segment 444 of the channel 146 within the flexible sheet 148 (FIG. 4). The second end 163a of the first wire 160a can be advanced to a desired first position within the circumferential segment 444, and the second end 163b of the second wire 160b can be advanced to a second position within the circumferential segment 444. As such, the second ends 163a, 163b of the wires 160a, 160b may be advanced to multiple first and/or second positions within the channel 146 until the desired or effective loop radius $R_L$ is achieved. In one embodiment, the second ends 163a, 163b may meet; however in other embodiments, the second ends 163a, 163b may not extend through the entire circumferential segment 444. In still other embodiments, the second ends 163a, 163b may overlap such that for at least a portion of the circumferential segment 444, the wires 160a, 160b overlap, for example to provide additional radial force or resilience within the overlapped region (not shown).

Referring to FIGS. 5A-5C together, the locking mechanism 170 can be any operator-controllable mechanical system that provides for the advancement or retraction of the wire(s) 160 through the channel 146 of the flexible sheet 148 of the inflow member 140. In some instances the locking mechanism 171 can provide for small incremental movements of the wire(s) 160 within the channel 146. In addition to advancement or retraction of the wire(s), and when deployed within the heart, the locking mechanism 170 may also be configured to maintain the wire 160 at a desired position within the channel 146 to maintain the inflow member 140 at the selected level of expansion, i.e., a desired loop radius $R_L$, within the patient's valvular area. For example, the locking mechanism 170 can be configured to prevent slippage or retraction of the wire(s) 160 proximally which could collapse the inflow member 140 following implantation. In one embodiment, the locking mechanism 170 can include a ratcheting mechanism 710 as described in more detail with respect to FIGS. 7-8D. In alternative arrangements, the locking mechanism 170 can include a screw or lock screw system. One of ordinary skill in the art will recognize other mechanical systems for advancing and/or retracting the wire(s) 160 or other elongated stiffening elements to radially expand and deploy the inflow member 140 during implantation.

FIG. 7 is an exploded view of a ratcheting mechanism 710 for use with the heart valve prosthesis 100 of FIG. 4 in accordance with an embodiment of the present technology. The ratcheting mechanism 710 includes a ratchet member 720 coupled to the wire(s) 160, a ratchet housing 730 at least partially surrounding the ratchet member 720, a ratchet tube 740 slideably disposed between the ratchet member 720 and the ratchet housing 730, and a slotted engagement tube 750 for engaging and moving the ratchet member 720 with respect to the ratchet housing 730. The ratchet housing 730 has opposing pawls 732a, 732b, 732c, 732d extending from a distal end 731 thereof. The ratchet member 720 includes a plurality of circumferential indentations 722 longitudinally spaced along a length $L_1$ of the ratchet member 720. The ratchet housing 730 is configured to be secured within the lumen 121 of the anchoring structure 120 as shown in FIGS. 4 and 5A-5C. In an embodiment hereof, the ratchet housing 730 is positioned along an inner circumference of the anchoring structure 120 so as to position the ratcheting mechanism 710 out of the blood flow passing through the lumen 121. The circumferential indentations 722 are configured to interact with the opposing pawls 732a, 732b, 732c, 732d of the ratchet housing 730 in order to permit linear movement of the ratchet member 720 within and relative to the ratchet housing 730 in only a first direction (e.g., distally). In this embodiment, the wire 160 is securely coupled the ratchet member 720 at a distal portion 721 thereof, and such linear motion of the ratchet member 720 in the distal direction thereby translates to distal movement of the wire 160 (e.g., within the channel 146; FIG. 4).

FIGS. 8A-8D are enlarged sectional views of the ratcheting mechanism 710 of FIG. 7 illustrating portions of a process for engaging the ratcheting mechanism 710 to deploy or retract the inflow member 140 of the heart valve prosthesis 100 of FIG. 4 in accordance with an embodiment of the present technology. FIG. 8A illustrates of a first position of the ratcheting mechanism 710 during deployment of the prosthesis 100, and particularly deployment of the inflow member 140. In this position (and during percutaneous delivery of the prosthesis 100), the ratchet member 720 is disposed within the ratchet housing 730 and tips 734a, 734c of the opposing pawls 732a, 732c are substantially aligned with the distal portion 721 of the ratchet member 720. It should be understood from the cross-sectional views shown in FIGS. 8A-8D that opposing pawls 732b, 732d shown in FIG. 7 would also include tips that act in the same manner as described herein for tips 734a, 734c of opposing pawls 732a, 732c. The wire 160 is secured within a lumen 726 of the ratchet member 720 and extends distally beyond the distal portion 721 thereof. In various arrangements, the wire 160 may be secured within the lumen 726 via adhesive, compression fit, or other mechanical means such as locking pin or screw.

A slotted tip 751 of the engagement tube 750, shown enlarged in FIG. 7A, has opposing longitudinal slots 753a, 753b between which extend opposing engagement levers 752a, 752b that are seated within a proximal most indentation 724 within a proximal portion 725 of the ratchet member 720. When not contained or biased inward by ratchet tube 740, each of the opposing engagement levers 752a, 752b may be configured to spread apart from the corresponding opposing lever and in a radially outward position so as to facilitate release of the ratchet member 720 when deployment is complete (described in more detail with respect to FIG. 8C). In the illustrated embodiment, the ratchet tube 740 is configured to surround the engagement tube 750 to maintain engagement of the opposing engagement levers 752a, 752b with the indentation 724 by restraining the opposing engagement levers 752a, 752b in a radially-inward or compressed orientation (see FIGS. 8A-8B, for example).

Referring to FIG. 8B, the wire 160 is advanced distally through distal movement (arrow $A_1$) of the ratchet member 720 with respect to the ratchet housing 730. Operatively, the engagement tube 750 is translated distally (e.g., by control through a deployment catheter described further herein) which pushes the ratchet member 720 in a forward or distal direction (arrow $A_1$). The opposing pawls 732a, 732b, 732c, 732d of the ratchet housing engage sequential circumferential indentations 722 (shown individually in FIG. 8B as 722a-722e) thereby permitting linear movement of the ratchet member 720 in the distal direction (arrow $A_1$) and inhibiting linear movement proximally. While five circumferential indentations 722 on the ratchet member 720 are illustrated in FIGS. 8A-8D, one of ordinary skill in the art will recognize that more than five indentations 722 or less than five indentions are possible. Likewise the ratchet member may have the length $L_1$ (FIG. 7) of any suitable length for translating distal movement to the wire(s) 160 as desired to deploy the inflow member 140 (FIG. 4). Furthermore, while four opposing pawls 732a, 732b, 732c, 732d on the ratchet housing 730 are illustrated, one of ordinary skill in the art will recognize that the ratchet housing 730 is not limited to four opposing pawls and that that the ratchet housing can have any number of pawls (e.g., greater or lesser than four) circumferentially positioned about the distal end 731 of the ratchet housing 730 without departing from the scope hereof.

Upon full deployment of the inflow member 140 (FIG. 4), the ratchet mechanism 710 can be disengaged by the delivery catheter system (not shown) in a manner that allows the ratchet member 720 to be maintained (e.g., locked) at a desired position with respect to the ratchet housing 730 and while preventing slippage or retraction of the wire(s) 160 proximally. Referring to FIG. 8C, once the desired positioning of the wire(s) 160 is achieved, the ratchet tube 740 can be retracted proximally (arrow $A_2$) relative to the proximal portion 725 of the ratchet member 720 thereby allowing the opposing engagement levers 752a, 752b of the engagement tube 750 to return to their unbiased position (e.g., radially outward from the indentation 724 of the ratchet member 720). Upon release of the opposing engagement levers 752a, 752b of the engagement tube 750, the engagement tip can be disengaged from the ratchet member 720 and retracted proximally (arrow A₃). Once the ratchet tube 740 and the engagement tube 750 are disengaged from the prosthesis 100, the ratchet mechanism 710 is in a locked configuration (FIG. 8C) and remains so in vivo.

In certain instances, it may be desirable to adjust the positioning of the prosthesis 100 within the native anatomy during implantation and/or after implantation. For example, cardiac imaging (e.g., echocardiography, fluoroscopy, etc.) can be used to assess positioning and outcome (e.g., prevention of paravalvular leakage) of the implanted prosthesis 100 (FIG. 3), and such imaging tools can instruct clinicians to reposition the device and/or adjust the degree of inflow member 140 expansion for achieving effective implantation. Likewise, it may be desirable to remove and/or replace the prosthesis 100 after implantation and/or use thereof. Accordingly, the ratcheting mechanism 710 allows for re-engagement of the locked position either before or after full removal of the ratchet tube 740 and engagement tube 750 components. FIG. 8D illustrates a step in a repositioning process of the ratcheting mechanism 710 in accordance with one embodiment of the present technology.

Referring to FIG. 8D, the engagement tube 750 is positioned with respect to the ratchet member 720 such that the opposing engagement levers 752a, 752b are aligned with the proximal most indentation 724 and such that the ratchet tube 740 compresses the levers 752a, 752b to engage the indentation 724 as it is slideably moved distally (arrow A4). The ratchet tube 740 is shown slideably disposed between the ratchet housing 730 and the ratchet member 720 so as to disengage and/or inhibit engagement of the opposing pawls 732a, 732b, 732c, 732d with the circumferential indentations 722 of the ratchet member 720. In instances of repositioning the prosthesis 100, the ratchet tube 740 can lift or disengage the opposing pawls 732a, 732b, 732c, 732d from the circumferential indentation 722b previously engaged. Upon disengagement of the opposing pawls 732a, 732b, 732c, 732d of the ratchet housing 730, the ratchet member 720 can be retracted proximally (arrow A5) by operatively retracting the engagement tube 750, thereby retracting the wire(s) 160 and at least partially collapsing the inflow member 140 for repositioning and/or removal of the prosthesis 100 as described.

Referring to FIGS. 3-8D together, the prosthesis 100 is provided with means to adjust the radial force of the inflow member 140 using one or more wires 160 to incrementally and selectively expand the inflow member 140 to accommodate unique patient anatomy during implantation. Additionally, the locking mechanism 170 configured for use with the prosthesis to manipulate the wire(s) 160, can allow a clinician to reposition the inflow member 140 and/or the prosthesis 100 multiple times within the native valve until a desired position and level of expansion (e.g., of the inflow member 140) is achieved (e.g., to reduce instances of paravalvular leakage). Furthermore, and as described in more detail herein, the cross-sectional profile of the inflow member 140 in a delivery configuration can be relatively reduced when compared to conventional prosthetic implants, thereby facilitating delivery of the prosthesis 100 percutaneously. For example, the wire 160 is used to expand the inflow member 140 only after locating the prosthesis for deployment within the targeted native region of the heart, which contributes to the reduced cross-sectional profile during delivery.

Selected Systems and Methods for Delivery and Implantation of Prosthetic Heart Valve Devices Several suitable delivery and deployment methods are discussed herein and discussed further below; however, one of ordinary skill in the art will recognize a plurality of methods suitable to deliver the prosthesis 100 to the targeted native valve region (e.g., percutaneous, transcatheter delivery using retrograde or antegrade approaches). Additionally, one of ordinary skill in the art will recognize a plurality of methods suitable to deploy the prosthesis 100 from a compressed configuration for delivery to the expanded configuration illustrated in FIG. 4.

Figure 9A:
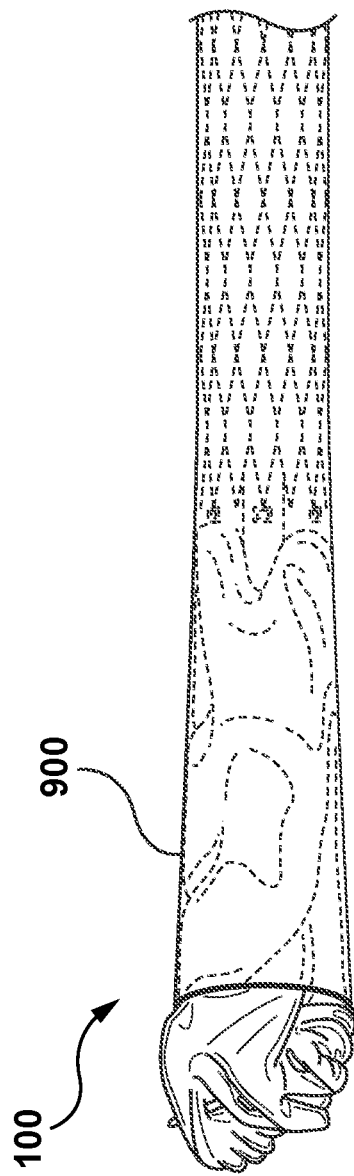
FIGS. 9A-9C are enlarged sectional views of a heart valve prosthesis illustrating steps of transition between a delivery configuration (e.g., low-profile or radially compressed state) and the deployed configuration (FIG. 4) in accordance with another embodiment of the present technology.
Figure 9B:
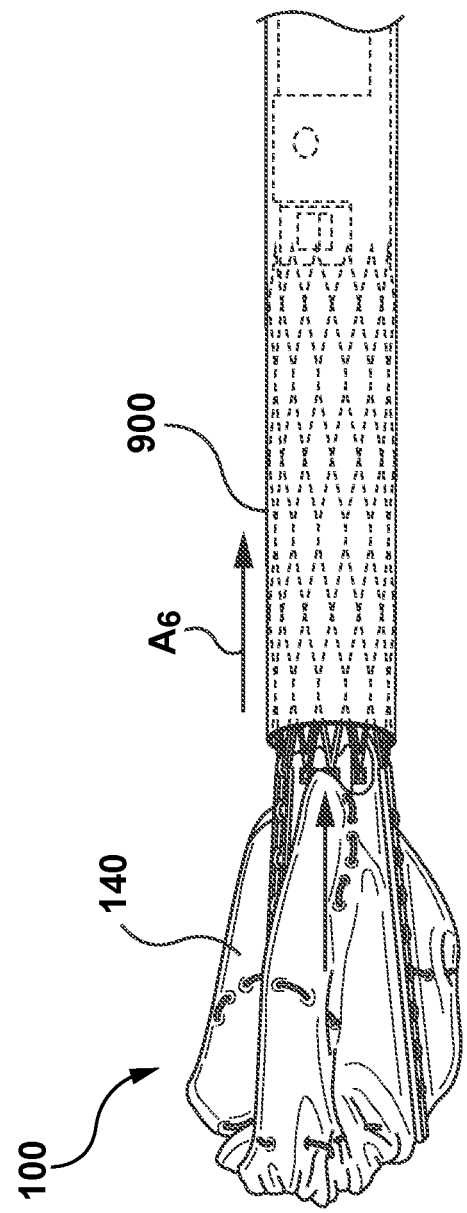
Figure 9C:
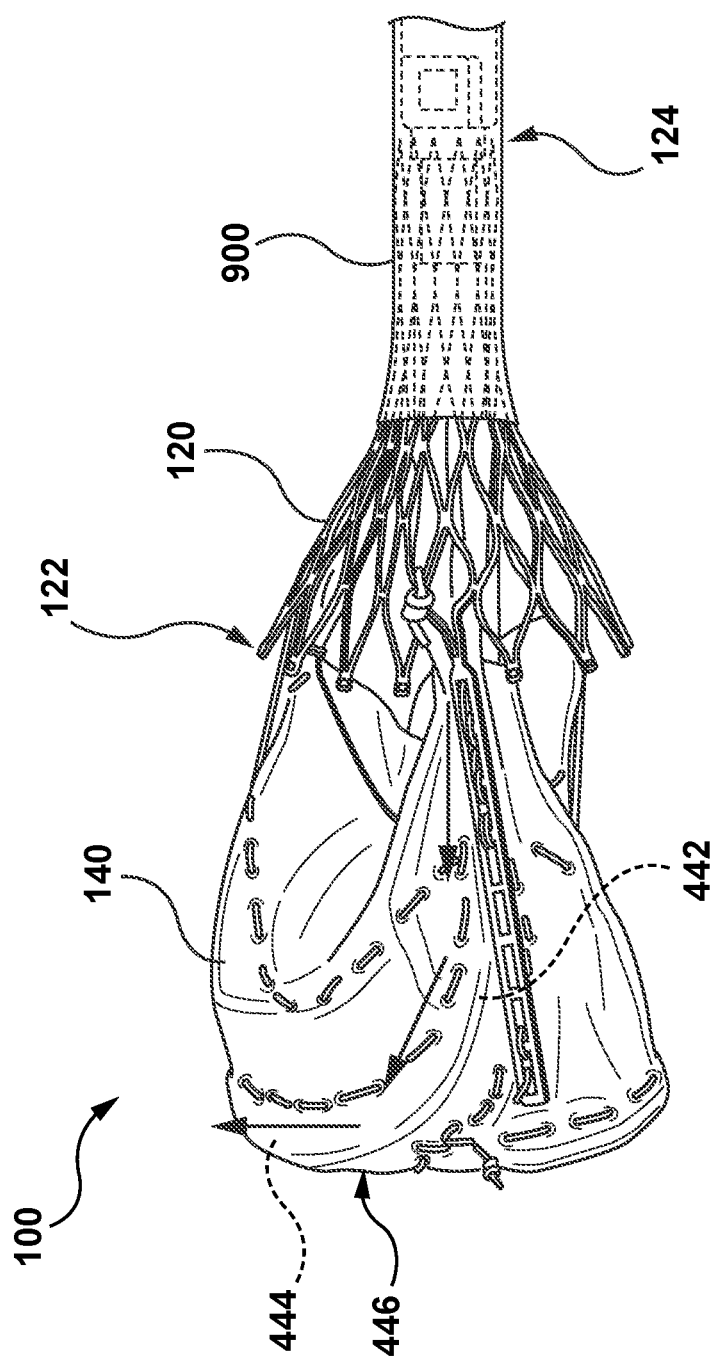

FIGS. 9A-9C are enlarged sectional views of a heart valve prosthesis 100 illustrating steps of transition between a delivery configuration (e.g., low-profile or radially compressed state) and the deployed or expanded configuration (FIG. 4) in accordance with another embodiment of the present technology. The heart valve prosthesis 100 can be movable between a compressed configuration (FIG. 9A) and an expanded configuration (FIG. 4) for deployment within the patient's heart. In the compressed configuration shown in FIG. 9A, the prosthesis 100 has a low profile retained as such by a delivery capsule or sheath 900 that together are suitable for delivery through small-diameter guide catheters (not shown) positioned in the heart via antegrade or retrograde approaches. As used herein, "expanded configuration" refers to the configuration of the prosthesis 100 when allowed to freely expand to an unrestrained size without the presence of constraining or distorting forces. "Deployed configuration," as used herein, refers to the prosthesis 100 once expanded at the native valve site (e.g., subject to the constraining and distorting forces exerted by the native anatomy) and once the inflow member 140 has been expanded with the wire(s) 160.

FIGS. 9B and 9C illustrate steps in the process of deploying the prosthesis 100 (e.g., such as at a native valve location). During deployment, the delivery sheath 900 is retracted proximally (arrow A6), first exposing the inflow member 140 within a first heart chamber or structure (e.g., the left ventricle) (FIG. 9B). Upon exposure of the inflow member 140 to the heart, the delivery sheath 900 is retracted further proximally releasing the first end 122 of the anchoring structure 120 (FIG. 9C). As shown in FIG. 9C, the wire 160 (see, e.g., FIG. 5A) is moved distally and within the longitudinal and circumferential segments 442, 444 of the channel 146 to expand inflow member 140, and in some embodiments, the inflow member is at least partially expanded and/or positioned prior to releasing the second end 124 of the anchoring structure 120 and allowing the anchoring structure to deploy and apply radial force against the native tissue. Once the delivery sheath 900 is fully retracted from the prosthesis 100, the prosthesis can remain in the deployed configuration (FIGS. 3 and 4). In certain embodiments, the delivery sheath 900 can reengage the prosthesis thereby transitioning the prosthesis from the deployed configuration to the delivery configuration (shown in FIG. 9A).

Figure 10:
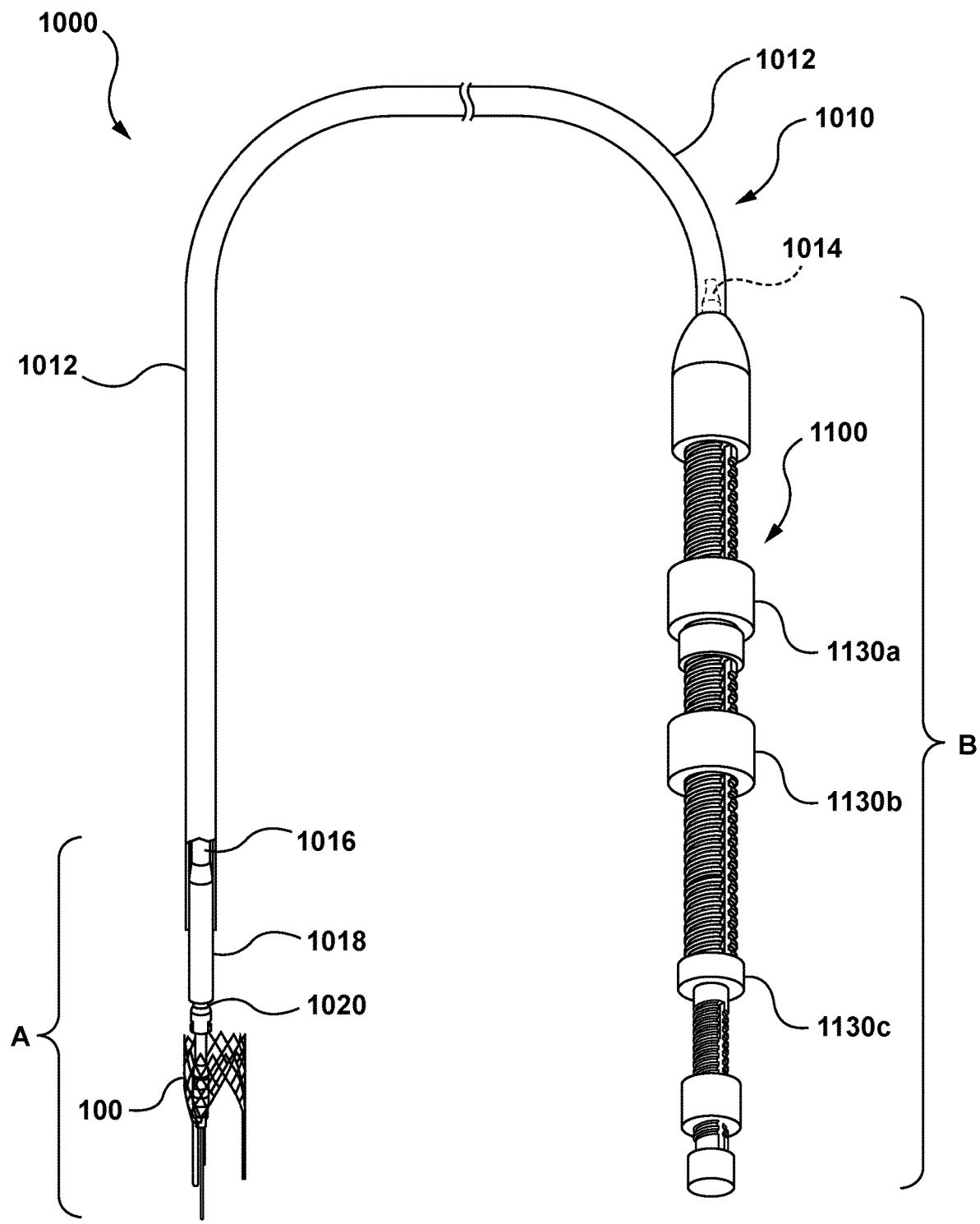
FIG. 10 is side partial cut-away view of a delivery system in accordance with an embodiment of the present technology.

FIGS. 10-11B illustrate one embodiment of a delivery system 1000 suitable for delivery of the heart valve prostheses disclosed herein. As used in reference to the delivery system, "distal" refers to a position having a distance farther from a handle of the delivery system 1000 along the longitudinal axis of the delivery system 1000, and "proximal"

refers to a position having a distance closer to the handle of the delivery system 1000 along the longitudinal axis of the delivery system 1000.

FIG. 10 is side partial cut-away view of one embodiment of the delivery system 1000 which may be used to deliver and deploy embodiments of the heart valve prosthesis 100 disclosed herein through the vasculature and to the heart of a patient. The delivery system 1000 may optionally include a guide catheter 1010 having a handle 1100 coupled to a delivery shaft 1012, which in some embodiments is 34F or less in diameter. The guide catheter 1010 may be steerable or pre-shaped in a configuration suitable for the particular approach to the target native valve. A delivery catheter 1014 is slideably disposed within the guide catheter 1010 and includes a flexible tubular outer shaft 1016 that extends to a delivery sheath 1018 (e.g., delivery sheath 900 of FIGS. 9A-9C) at a distal end thereof. During advancement to a treatment site, the prosthesis 100 is positioned in a compressed or delivery configuration within the delivery sheath 1018 as described above. A flexible inner shaft 1020 is positioned slideably within outer shaft 1016 and extends at least partially through the prosthesis 100. The prosthesis 100 is coupled to the inner shaft 1020 and is releasable from the inner shaft 1020 by release wires (not shown) that are configured to engage, for example, the coupling features 125 (FIG. 4) on the frame 110 of the prosthesis 100. Additionally, the engagement tube 750 and ratchet tube 740 extend through the inner shaft 1020 (illustrated in FIG. 11A and discussed further herein) to engage the ratcheting mechanism 710 secured within the anchoring structure 120 of the prosthesis 100. In the embodiment of FIG. 11 and with reference to FIG. 11A, the delivery sheath 1018 may further include a guidewire lumen 1019 attached or formed along only a distal length of the delivery sheath 1018 through which a guidewire (not shown) may be slideably positioned, such that the delivery sheath 1018 may be tracked through the vasculature in a rapid-exchange manner. In other embodiments in accordance herewith, other guidewire lumens are contemplated such as one that extends the length of the delivery system such that the delivery sheath and/or other catheter thereof may be used in an over-the-wire manner. The delivery sheath 1018 can protect and secure the prosthesis 100 in its compressed configuration during delivery (FIG. 9A). The delivery catheter 1014 is coupled to a plurality of actuator mechanisms 1130 (shown individually as 1130a-1130c) on the handle 1100 of the delivery catheter 1014.

FIG. 11A is an enlarged sectional view of the portion A and FIG. 11B is an enlarged sectional view of the portion B of the delivery system 1000 shown in FIG. 10 and in accordance with an embodiment of the present technology. FIG. 11A shows the distal end of the delivery catheter 1014 with the delivery sheath 1018 cut away to illustrate the coupling of the engagement tube 750 and ratchet tube 740 extending through and from the inner shaft 1020 to the ratcheting mechanism 710 secured within the anchoring structure 120 of the prosthesis 100. Operatively, the delivery sheath 1018 may be retracted relative to the prosthesis 100 to permit expansion of the prosthesis 100 while the inner shaft 1020 maintains the longitudinal position of the prosthesis 100 relative to the anatomy. The ratchet tube 740 and engagement tube 750 may be nested and extend proximally to the handle 1100, for example, within a designated lumen of the inner shaft 1020.

FIG. 11B shows a cross-section view of the handle portion 1100 of the delivery system including the actuator mechanisms 1130 which are configured to control one or more of the delivery elements at the distal end (FIG. 11A) of the delivery catheter 1014. Referring to FIGS. 11A and 11B together, the handle 1100 includes a first actuator mechanism 1130a suitable to control the advancement and retraction of the delivery sheath 1018. For example, during delivery of the prosthesis 100, the operator can engage the first actuator mechanism 1130a to begin retraction of the delivery sheath 1018 from the prosthesis 100 in steps as described previously with respect to FIGS. 9A-9C. In this way, the outer shaft 1016 may be retracted relative to the inner shaft 1020 to release (e.g., deploy) the prosthesis 100 from the delivery sheath 1018.

Referring to FIGS. 11A and 11B together, the handle 1100 also includes a second actuator mechanism 1130b configured to control advancement (distally) and retraction (proximally) of the engagement tube 750 within the inner shaft 1020 of the delivery catheter 1014. The handle 1100 further includes a third actuator mechanism 1130c configured to control advancement (distally) and retraction (proximally) of the ratchet tube 740 within the inner shaft 1020 of the delivery catheter 1014. Together, the second and third actuator mechanisms 1130b, 1130c can be used to engage the ratcheting mechanism 710 with the engagement tube 750 as shown in FIGS. 8A-8D. For example, the second actuator mechanism 1130b can be used to operatively move the engagement tube 750 such the opposing engagement levers 752a, 752b are aligned with indentation 724 of the ratchet member 720. The third actuator mechanism 1130c can then be used to operatively advance the ratchet tube 740 over the opposing engagement levers 752a, 752b to bias them to engage the indentation 724 (FIGS. 8A and 8B). Then, the second and third actuator mechanisms 1130b, 1130c can be used to advance the ratchet member 720 distally thereby translating distal movement of the wire 160 within the channel 146 of the inflow member 140 (FIG. 9C). Once the inflow member 140 is suitably expanded, the second and third actuator mechanisms 1130b, 1130c can be operated to disengage the engagement tube 750 from the ratcheting mechanism 710 secured within the prosthesis 100 by retracting these components proximally through the inner shaft 1020.

Various actuator mechanisms 1130 can be used, such as an axially-slidable lever, a rotatable rack and pinion gear, or other known mechanisms. In certain embodiments, a suitable mechanism (not shown) on the handle 1100 can allow the operator to manage release wires (not shown) configured to couple the prosthesis 100 to the delivery catheter 1014 via the coupling features 125. Once deployed, the suitable mechanism can be engaged to retract the release wires in a proximal direction until they are disengaged from the coupling features 125. Following device deployment, the delivery catheter 1014 and guide catheter 1012 can be retracted through the vasculature and removed from the patient.

Image guidance, e.g., intracardiac echocardiography (ICE), fluoroscopy, computed tomography (CT), intravascular ultrasound (IVUS), optical coherence tomography (OCT), or another suitable guidance modality, or combination thereof, may be used to aid the clinician's positioning and manipulation of the prosthesis 100 at the target native valve region. In some embodiments, image guidance components (e.g., IVUS, OCT) can be coupled to the distal portion of the delivery catheter 1014, guide catheter 1010, or both to provide three-dimensional images of the vasculature proximate to the target heart valve region to facilitate positioning and/or deployment of the prosthesis 100 within the heart valve region.

Figure 12:
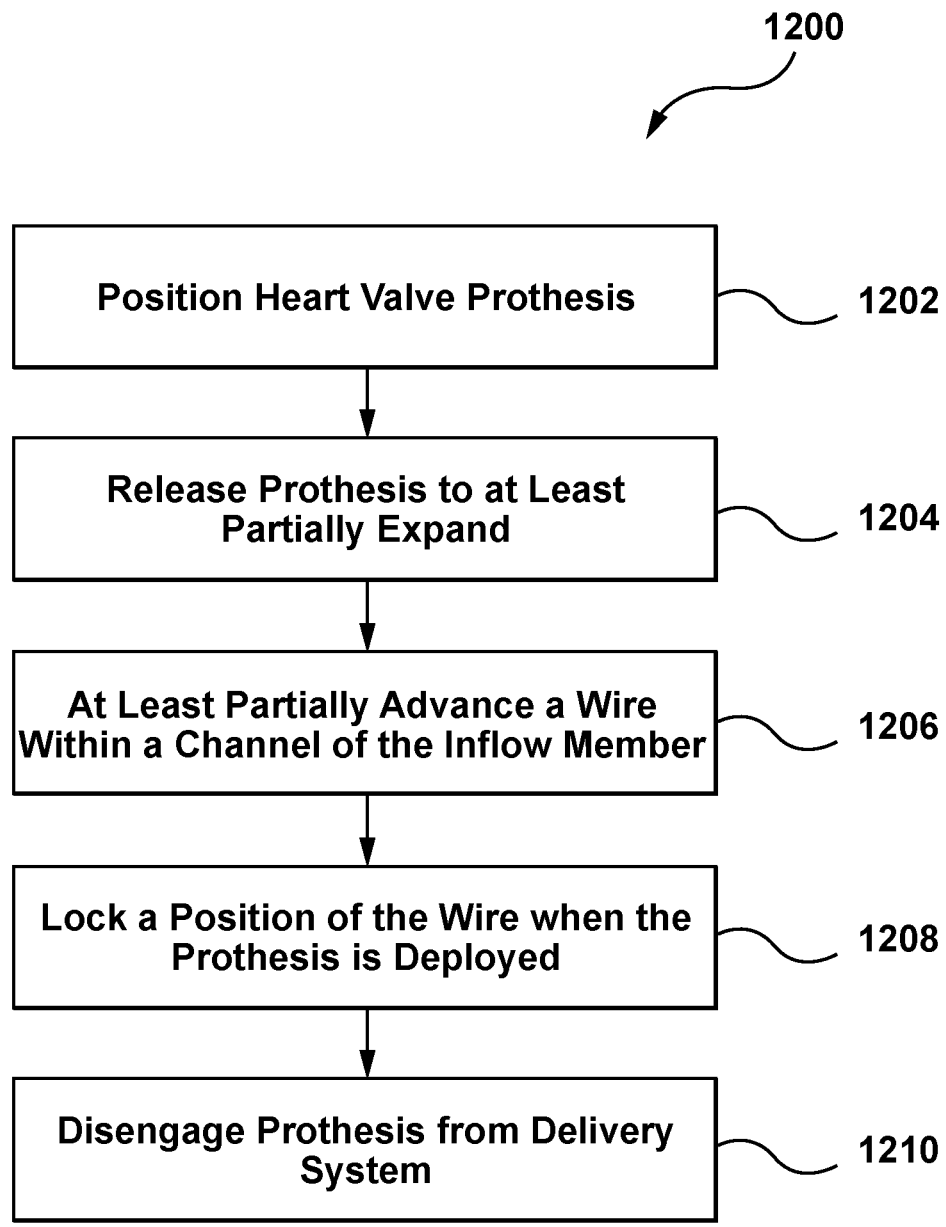
FIG. 12 is flow diagram illustrating a method for repairing or replacing a heart valve of a patient in accordance with an embodiment of the present technology.

FIG. 12 is block diagram illustrating a method 1200 for repairing or replacing a heart valve of a patient with the heart valve prosthesis 100 described above with reference to FIGS. 3-11B and in accordance with an embodiment of the present technology. Referring to FIG. 12 (and with additional reference to FIGS. 3-11B), the method 1200 can include positioning a heart valve prosthesis 100 having a compressed configuration within a native heart valve region of the patient (block 1202). The method 1200 can also include releasing the prosthesis 100 to at least partially expand (block 1204). In one embodiment, the prosthesis 100 can at least partially expand when a delivery sheath 1018 is retracted, thereby removing the radially inward constraint on the prosthesis. The prosthesis 100 may be positioned such that an inflow member 140 extends through an annulus of the heart valve (e.g., the aortic valve).

The method 1200 can further include at least partially advancing a wire 160 within a channel 146 of the inflow member 140 to transition the inflow member 140 into a deployed (e.g., radially expanded) configuration (block 1206). In one embodiment, the wire 160 (or plurality of wires) can be advanced with operation of a locking mechanism 170, such as a ratcheting mechanism 710, secured within a lumen 121 of the prosthesis 100. For example, when using a ratcheting mechanism 710 as described herein, the wire 160 can be advanced incrementally (e.g., in either large, small, or a combination of large and small increments). In certain embodiments, the advancement of the wire 160 using the locking mechanism 170 can be reversed such that the wire 160 is retracted, for example, to adjust radial expansion of the inflow member 140, reposition the prosthesis 100, or remove the prosthesis 100 from the patient's heart 10. In alternative embodiments, the wire 160 may be advanced through use of an actuator mechanism 1130 disposed on the handle 1100 of the guide catheter 1010.

The method 1200 can still further include locking a position of the wire 160 when the deployed configuration of the inflow member 140 is achieved (block 1208). In one embodiment, locking the wire 160 includes inhibiting slippage or retraction of the wire 160 proximally, thereby preventing collapse of the inflow member 140. In a particular embodiment, the locking mechanism 170 (e.g., the ratcheting mechanism 710) can be configured to temporarily, permanently, or reversibly lock the position of the wire 160 at a desired level of advancement that expands the inflow member 140 in a manner that allows the inflow member 140 to adequately engage the native tissue to inhibit paravalvular leakage between the prosthesis 100 and the region of implantation (e.g., native heart valve region, previously implanted prosthetic heart valve device or stent, etc.). When the inflow member 140 is deployed, the method 1200 may continue with releasing remaining portions of the prosthesis 100, such as the anchoring structure 120, to self-expand or otherwise deploy (if not yet completed) and/or disengaging the prosthesis from the delivery system 1000 (block 1210). The prosthesis 100 may be positioned such that the anchoring structure 120 of the frame 110 is in a subannular position and will provide radial force outward against a wall of the native heart valve region when in the deployed configuration. In a particular example, the anchoring structure 120 can be in a region of the ascending aorta downstream of the sinotubular junction.

Additional Embodiments

Features of the heart valve prosthesis and delivery system components described above and illustrated in FIGS. 3-11B can be modified to form additional embodiments configured in accordance with the present technology. For example, the delivery system 1000 can provide delivery of any of the heart valve prosthesis 100 illustrated in FIGS. 3-9C using one or more additional delivery elements such as straightening sheaths and/or guide wires controllable, for example, using the handle 1100. Similarly, the heart valve prosthesis described above and illustrated in FIGS. 3-9C showing only a single wire 160 or locking mechanism 170 can also include additional wires and similar or different locking mechanisms positioned within the prosthesis 100 or, alternatively, within the handle 1100. Additionally, while the heart valve prosthesis 100 described above shows a single flexible inflow member housing the prosthetic valve component 150, it will be understood that the prosthesis 100 can include additional support structures (e.g. cylindrical support structures) for housing the prosthetic valve component 150 within or downstream of the inflow member 140.

Various method steps described above for delivery and deployment of the heart valve prosthesis for repairing or replacing a heart valve of a patient also can be interchanged to form additional embodiments of the present technology. For example, while the method steps described above are presented in a given order, alternative embodiments may perform steps in a different order. The various embodiments described herein may also be combined to provide further embodiments.

While various embodiments have been described above, it should be understood that they have been presented only as illustrations and examples of the present technology, and not by way of limitation. It will be apparent to persons skilled in the relevant art that various changes in form and detail can be made therein without departing from the spirit and scope of the present technology. Thus, the breadth and scope of the present technology should not be limited by any of the above-described embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:
1. A heart valve prosthesis for implantation at a native valve region of a heart, the prosthesis comprising:
   an expandable frame defining a lumen through which blood may flow, the lumen extending from a first end to a second end thereof, wherein the frame includes a plurality of commissure posts extending from the first end;
   a tubular component attached to the plurality of commissure posts, the tubular component having a first portion and a second portion and a channel formed in a wall thereof, wherein an interior of the tubular component is configured to support a prosthetic valve;
   a locking mechanism secured within the lumen of the expandable frame; and
   a wire operably coupled to the locking mechanism, the wire being at least partially slideably disposed within the channel of the tubular component, wherein the locking mechanism is configured to permit the wire to be advanced within the channel of the tubular component to thereby transition the tubular component into a deployed configuration.

2. The heart valve prosthesis of claim 1, wherein the channel extends from at least the second portion to the first portion.

3. The heart valve prosthesis of claim 1, wherein the tubular component comprises a flexible sheet having opposed inner and outer layers that form the wall of the tubular component and between which the channel is defined.

4. The heart valve prosthesis of claim 3, wherein the channel includes a circumferential segment that at least partially surrounds an opening of the tubular component at the first portion.

5. The heart valve prosthesis of claim 4, wherein a fold of the flexible sheet extends between the inner and outer layers, and the fold encircles the opening at the first portion of the tubular component to define at least a portion of the circumferential segment of the channel.

6. The heart valve prosthesis of claim 4, wherein the channel includes a longitudinal segment that extends from the circumferential segment to the second portion of the tubular component.

7. The heart valve prosthesis of claim 6, wherein the wire extends from the locking mechanism through the longitudinal segment and at least partially through the circumferential segment of the channel, and wherein a first end of the wire is coupled to the locking mechanism and a second end of the wire is secured within the circumferential segment.

8. The heart valve prosthesis of claim 6, wherein the wire has first and second wire ends coupled to the locking mechanism, and wherein a portion of the wire between the first and second ends is slidably disposed within the longitudinal and circumferential segments to form a loop.

9. The heart valve prosthesis of claim 8, wherein a radius of the loop is configured to increase or decrease by advancing or retracting at least one of the first or second wire ends.

10. The heart valve prosthesis of claim 1, wherein the locking mechanism is a ratcheting mechanism.

11. The heart valve prosthesis of claim 10, wherein the ratcheting mechanism is configured to permit a ratchet member to be retracted relative to a housing in order to at least partially retract the wire from the channel of the tubular component to thereby transition the tubular component into a reduced-diameter configuration.

12. A system for repair or replacement of a heart valve, the system comprising:
   a prosthetic heart valve comprising,
      an anchoring structure,
      a tubular component coupled to and extending from the anchoring structure, the tubular component defining a lumen and having a channel within a wall thereof,
      a prosthetic valve component disposed within the lumen of the tubular component, the prosthetic valve component configured to inhibit retrograde blood flow through the lumen,
      an elongated stiffening element at least partially disposed within the channel of the tubular component to thereby transition the tubular component and the prosthetic valve component into a deployed configuration, and
      a locking mechanism secured to the anchoring structure and coupled to the stiffening element; and
   a catheter assembly configured to deliver and deploy the prosthetic heart valve, the catheter assembly comprising,
      a handle assembly having a first actuator for operating the locking mechanism to advance the stiffening element within the channel of the tubular component, and
      an engagement tube extending from the handle assembly, the engagement tube configured to operatively engage the locking mechanism at a proximal end thereof upon actuation of the first actuator.

13. The system of claim 12, wherein the stiffening element is configured to be at least partially retracted from the channel of the tubular component to thereby transition the tubular component and the prosthetic valve component into a reduced-diameter configuration.

14. The system of claim 12, wherein the prosthetic heart valve further comprises a plurality of commissure posts extending from the anchoring structure, and wherein the tubular component comprises a sheet of flexible material coupled to the commissure posts.

15. The system of claim 12, wherein the stiffening element at least partially disposed within the channel of the tubular component is structurally independent of the anchoring structure, and wherein the stiffening element is radially deformable without substantially deforming the anchoring structure.

16. The system of claim 12, wherein the stiffening element extends from the locking mechanism through the channel to form a loop.

17. The system of claim 12, wherein a first end of the stiffening element is coupled to the locking mechanism and a second end of the stiffening element is secured within the channel.

18. The system of claim 12, wherein the tubular component comprises a folded sheet of flexible material that forms opposed inner and outer layers of the wall of the tubular component between which the channel is defined.

19. The system of claim 18, wherein the channel includes a circumferential segment that at least partially surrounds an opening of the lumen of the tubular component.

20. The system of claim 12, wherein the locking mechanism is a ratcheting mechanism.

* * * * *